(12) United States Patent
Makrigiorgos

(10) Patent No.: US 8,455,190 B2
(45) Date of Patent: Jun. 4, 2013

(54) ENRICHMENT OF A TARGET SEQUENCE

(75) Inventor: Gerassimos Makrigiorgos, Chestnut Hill, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 372 days.

(21) Appl. No.: 12/671,295

(22) PCT Filed: Jul. 31, 2008

(86) PCT No.: PCT/US2008/009248
§ 371 (c)(1),
(2), (4) Date: Mar. 18, 2010

(87) PCT Pub. No.: WO2009/017784
PCT Pub. Date: Feb. 5, 2009

(65) Prior Publication Data
US 2010/0203532 A1 Aug. 12, 2010

Related U.S. Application Data

(60) Provisional application No. 60/962,838, filed on Aug. 1, 2007.

(51) Int. Cl.
*C12Q 1/68* (2006.01)
*C07H 21/00* (2006.01)
*C07H 21/02* (2006.01)
*C07H 21/04* (2006.01)

(52) U.S. Cl.
USPC .......... 435/6.1; 536/22.1; 536/23.1; 536/24.3

(58) Field of Classification Search
USPC ........................ 435/6.1; 536/22.1, 23.1, 24.3
See application file for complete search history.

(56) References Cited

U.S. PATENT DOCUMENTS

| | | | |
|---|---|---|---|
| 4,458,066 A | 7/1984 | Caruthers et al. | |
| 4,683,195 A | 7/1987 | Mullis et al. | |
| 4,683,202 A | 7/1987 | Mullis | |
| 4,800,159 A | 1/1989 | Mullis et al. | |
| 5,045,450 A * | 9/1991 | Thilly et al. | 435/6.1 |
| 5,075,217 A | 12/1991 | Weber | |
| 5,399,491 A | 3/1995 | Kacian et al. | |
| 5,409,818 A | 4/1995 | Davey et al. | |
| 5,427,930 A | 6/1995 | Birkenmeyer | |
| 5,554,527 A | 9/1996 | Fickenscher | |
| 5,618,703 A | 4/1997 | Gelfand et al. | |
| 5,631,147 A | 5/1997 | Lohman et al. | |
| 5,648,211 A | 7/1997 | Fraiser et al. | |
| 5,744,311 A | 4/1998 | Fraiser et al. | |
| 5,792,607 A | 8/1998 | Backman et al. | |
| 5,846,710 A | 12/1998 | Bajaj | |
| 5,849,497 A | 12/1998 | Steinmann | |
| 6,030,115 A | 2/2000 | Ishiguro et al. | |
| 6,174,680 B1 | 1/2001 | Makrigiorgos | |
| 6,197,499 B1 | 3/2001 | Hughes | |
| 7,635,566 B2 * | 12/2009 | Brenner | 435/6.18 |
| 2002/0016680 A1 * | 2/2002 | Wang et al. | 702/19 |
| 2003/0008286 A1 * | 1/2003 | Zou et al. | 435/6 |
| 2006/0063175 A1 | 3/2006 | Xu et al. | |
| 2007/0020672 A1 | 1/2007 | Wittwer et al. | |
| 2007/0154892 A1 | 7/2007 | Wain-Hobson et al. | |

FOREIGN PATENT DOCUMENTS

| | | |
|---|---|---|
| EP | 0370719 | 5/1990 |
| JP | 2005-518216 | 6/2005 |
| WO | 9011369 | 10/1990 |
| WO | 9013668 | 11/1990 |
| WO | 9114003 | 9/1991 |
| WO | 9719193 | 5/1997 |
| WO | 9914226 | 3/1999 |
| WO | 03/072809 | 9/2003 |
| WO | 2009/017784 | 2/2009 |
| WO | 2009/019008 | 2/2009 |

OTHER PUBLICATIONS

Coutelle, C. New DNA-Analysis techniques (Minireview). Biomed. Biochm.Acta 50: 1, 3-10(1991).*
Frommer et al. A genomic sequencing protocol that yields a positive display of 5-methylcytosine residues in individual DNA strands. PNAS 89:1827 (1992).*
Jeffreys et al. DNA enrichment by allele-specific hybridization (DEASH): a novel method for haplotyping and for detecting low-frequency base substitutional variants and recombinant DNA molecules. Genome Research 13:1216(2003).*
Li-Sucholeiki et al. A Sensitive Scanning Technology for Low Frequency Nuclear Point Mutations in Human Genomic DNA. Nucleic Acids Research 28(9) : e44 (2000).*
Giesendorf et al. Molecular Beacons : a new approach for semiautomated mutation analysis. Clinical Chemistry 44(3) :482 (1998).*
Liu et al .Denaturing high performance liquid chromatography (DHPLC) used in the detection of germline and somatic mutations. Nucleic Acids Research 26(6) :1396 (1998).*
Liu et al.,Detection of hotspot mutations and polymorphisms using an enhanced PCR-RFLP approach. Human Mutation 21 :535 (2003).*
Makrigiorgos GM. PCR-based detection of minority point mutations. Human Mutations 23 : 406 (2004).*
Orita et al., Rapid and sensitive detection of point mutations and DNA polymorphisms using the polymerase chain reaction. Genomics 5 :874-879 (1989).*
Persson et al. Four-color multiplex reverse transcription polymerase chain reaction—Overcoming its limitations. Analytical Biochemistry 344 : 33 (2005).*
Sanchez et al. Two-temperature LATE-PCR endpoint genotyping. BMC Biotechnology 6(44) 14 pages (Dec. 2006).*
Till et al. High- throughput discovery of rare human nucleotide polymorphisms by EcoTILLING . Nucleic Acids Research 34(13) : e99 (2006).*

(Continued)

*Primary Examiner* — Ethan C Whisenant
(74) *Attorney, Agent, or Firm* — Andrus, Sceales, Starke & Sawall, LLP

(57) ABSTRACT

The present invention is directed to methods, compositions, software and devices for enriching low abundance alleles from a sample. The method is based in part on a modified nucleic acid amplification protocol that includes incubating the reaction mixture at a critical denaturing temperature or "Tc". By employing the present invention the current detection limits of all PCR-based technologies are greatly improved.

26 Claims, 11 Drawing Sheets

OTHER PUBLICATIONS

Liew et al., "Genotyping of Single-Nucleotide Polymorphisms by High-Resolution Melting of Small Amplicons", Clinical Chemistry (2004), vol. 50(7), pp. 1156-1164, Esp., Abstract, p. 1745, para. 5, p. 1157.

Lipsky et al., DNA Melting Analysis for Detection of Single Nucleotide Polymorphisms, Mol. Diag. Gen. (2001), vol. 47, pp. 635-644.

"High-throughput oncogene mutation profiling in human cancer", Roman K. Thomas et al., Nature Genetics, vol. 39, No. 3, Mar. 2007, pp. 347-351.

"A Comparison of High-Resolution Melting Analysis with Denaturing High-Performance Liquid Chromatography for Mutation Scanning—Cystic Fibrosis Transmembrane Conductance Regulator Gene as a Model", Lan-Szu Chou, Ph.D. et al., Am J Clin Pathol 2005, vol. 124, pp. 339-338.

"Sensitive mutation detection in heterogeneous cancer specimens by massively parallel picoliter reactor sequencing", Roman K. Thomas et al., Nature Medicine, vol. 12, No. 7, Jul. 2006; pp. 852-855.

"EGFR Mutations in Lung Cancer: Correlation with Clinical Response to Gefitinib Therapy", J. Guillermo Paez, Sciencexpress, Apr. 29, 2004; vol. 304, pp. 1497-1500.

"A Rapid and Sensitive Enzymatic Method for Epidermal Growth Factor Receptor Mutation Screening", Pasi A. Janne et al., Clin Cancer Res 2006, vol. 12, No. 3, Feb. 1, 2006, pp. 751-758.

"Allelic dilution obscures detection of a biologically significant resistance mutation in EGFR-amplified lung cancer", Jeffrey A. Engelman et al., The Journal of Clinical Investigation, vol. 116, No. 10, Oct. 2006, pp. 2695-2706.

"Detection and quantification of mutations in the plasma of patients with colorectal tumors", Frank Diehl et al., Proc. Natl Acad Sci USA, vol. 102, No. 45, Nov. 8, 2005, pp. 16368-16373.

"Mutant DNA in Plasma of Lung Cancer Patients, Potential for Monitoring Response to Therapy", Tatsuo Kimura et al., Ann NY Acad Sci, vol. 1022, 2004, pp. 55-60.

"Detection of tumor mutations in the presence of excess amounts of normal DNA", Xiyuan Sun et al., Nature Biotechnology, vol. 19, Feb. 2002, pp. 186-189.

"Detection of Rare Mutant Alleles by Restriction Endonuclease-mediated Selective-PCR: Assay Design and Optimization", Caroline J. Fuery et al., Clinical Chemistry, vol. 46, No. 5, Feb. 28, 2000, pp. 620-624.

"Methods for detection of point mutations: performance and quality assessment", Peter Nollau et al., Clinical Chemistry, vol. 43, No. 7, Mar. 4, 1997, pp. 1114-1128.

"Enzymatic mutation detection technologies", Anthony T. Yeung et al., BioTechniques, vol. 38, No. 5, May 2005, pp. 749-758.

"High-throughput genotyping assay approaches", Pui-Yan Kwok, Pharmacogenomics, vol. 1, No. 1, 2000 Ashley Publications Ltd., pp. 95-100.

"Finding a Needle in a Haystack:Detection and Qualification of Rare Mutant Alleles Are Coming of Age", Pui-Yan Kwok, clinical Chemistry, vol. 46, No. 5, 2000, pp. 593-594.

"High-Resolution Genotyping by Amplicon Melting Analysis Using LCGreen", Carl T. Wittwer et al., Clinical Chemistry, vol. 49, No. 6, Mar. 11, 2003, pp. 853-860.

"Sensitivity and Specificity of Single-Nucleotide Polymorphism Scanning by High-Resolution Melting Analysis", Gudrun H. Reed et al., Clinical Chemistry, vol. 50, No. 10, Jul. 14, 2004, pp. 1748-1754.

"Genome Sequencing in Open Microfabricated High Density Picoliter Reactors", Marcel Margulies et al., Nature, vol. 437, No. 7057, Sep. 15, 2005, pp. 376-380.

"Novel non-isotopic detection of MutY enzyme-recognized mismatches in DNA via ultrasensitive detection of aldehydes", Gautam Maulik et al., Nucleic Acids Research, vol. 27, No. 5, Jan. 15, 1999, pp. 1316-1322.

"Highly Selective Isolation of Unknown Mutations in Diverse DNA Fragments: Toward New Mutiplex Screening in Cancer", Subrata Chakrabarti et al., Cancer Research, vol. 60, Jul. 15, 2000, pp. 3732-3737.

"Detection of Hotspot Mutations and Polymorphisms Using an Enhanced PCR-RFLP Approach", W. H. Liu et al., Human Mutation, vol. 21, Dec. 4, 2002, pp. 535-541.

"Inverse PCR-Based RFLP Scanning Identifies Low-Level Mutation Signatures in Colon Cells and Tumors", Wei-Hua Liu et al., Cancer Research, vol. 64, Apr. 1, 2004, pp. 2544-2551.

"s-RT-MELT for rapid mutation scanning using enzymatic selection and real time DNA-melting: new potential for multiplex genetic analysis", Jin Li et al., Nucleic Acids Research, vol. 35, No. 12, Jun. 1, 2007, pp. 1-11.

"Mutations in exon 7 and 8 of p53 as poor prognostic factors in patients with non-small cell lung cancer", Cheng-long Huang et al., Oncogene, vol. 16, Dec. 9, 1997, pp. 2469-2477.

"p53 Mutations and Survival in Stage I Non-Small-Cell Lung Cancer: Results of a Prospective Study", Steven A. Ahrendt et al., Journal of the National Cancer Institute, vol. 95, No. 13, Jul. 2, 2003, pp. 961-970.

Li, Jin et al.: Coamplification at Lower Denaturation Temperature-PCR Increases Mutation-Detection Selectivity of TaqMan-Base Real-Time PCT, Clinical Chemistry, vol. 55, No. 4, Apr. 2009, pp. 748-756.

Li, Jin et al.: Cold-PCT: a new platform for highly improved mutation detection in cancer and genetic testing, Biochemical Society Transactions, Portland Press Ltd., GB, vol. 37, No. Pt. 2, Apr. 1, 2009, pp. 417-432.

Dominguez, Patrick L. et al.: Wild-type blocking polymerase chain reaction for detection of single nucleotide minority mutations from clinical specimens, Oncogene, Nature Publishing Group, GB, vol. 24, No. 45, Oct. 1, 2005, pp. 6830-6834.

Milbury, Coren A. et al.: Ice-Cold-PCR enables rapid amplification and robust enrichment for low-abundance unknown DNA mutations, Nucleic Acids Research, Jan. 1, 2011, LNKD-PUBMED: 20937629, vol. 39, No. 1, E2, Oct. 11, 2010, pp. 1-10.

Worm, Jesper et al.: In-Tube DNA Methylation Profiling by Fluorescence Melting Curve Analysis, Clinical Chemistry, vol. 47, No. 7, pp. 1183-1189.

Botstein, David et al.: Constructionn of a Genetic Linkage Map in Man Using Restriction Fragment Length Polymorphisms, Am J Hum Genet, vol. 32, 1980, pp. 314-331.

Lander, Eric S. et al.: Mapping Mendelian Factors Underlying Quantitative Traits Using RFLP Linkage Maps, Genetics, vol. 121, Jan. 1989, pp. 185-199.

Kulinski, T. et al.: Comparative calorimetric studies on the dynamic conformation of plant 5S rRNA: II structural interpretation of the thermal unfolding patterns for lupin seeds and wheat germ, Nucleic Acids Research, vol. 19, No. 9, Apr. 11, 1991, pp. 2449-2455.

Kaneshisa, Minoru: Use of statistical criteria for screening potential homologies in nucleic acid sequences, Nucleic Acid Research, vol. 12, No. 1, 1984, pp. 203.

Orum, Henrik et al.: Single base pair mutation analysis by PNA directed PCR clamping, Nucleic Acids Research, 1993, vol. 21, No. 23, pp. 5332-5336.

Armour, John A.L. et al.: Recent advances in minisatellite biology, FEBS Letters, vol. 307, No. 1, Jul. 1992, pp. 113-115.

Aoki, Kazunori et al.: Liposome-mediated in Vivo Gene Transfer of Antisense K-ras Construct Inhibits Pancreatic Tumor Dissemination in the Murine Peritoneal Cavity, Cancer Research, vol. 55, Sep. 1, 1995, pp. 3810-3816.

Pearson, William R. et al.: Improved tools for biological sequence comparison, Proc. Natl. Acad. Sci. USA, vol. 85, Apr. 1988, pp. 2444-2448.

Altschul, Stephen F. et al.: Gapped BLAST and PSI-BLAST: a new generation of protein database search programs, Nucleic Acids Research, 1997, vol. 25, No. 17, pp. 3389-3402.

Henikoff, Steven et al.: Amino acid substitution matrices from protein blocks, Proc. Natl. Acad. Sci. USA, vol. 89, Nov. 1992, pp. 10915-10919.

Karlin, Samuel et al.: Applications and statistics for multiple high-scoring segments in molecular sequences, Proc. Natl. Acad. Sci. USA, vol. 90, pp. 5873-5877.

Gyllensten, Ulf B. et al.: Generation of single-stranded DNA by the polymerase chain reaction and its application to direct sequencing of the HLA-DQA locus, Proc. Natl. Acad. Sci. USA, vol. 85, Oct. 1988, pp. 7652-7656.

Walker, G.T. et al.: Strand displacement amplification-an isothermal, in vitro DNA amplification technique, Nucleic Acids Research, vol. 20, No. 7, Mar. 10, 1992, pp. 1691-1696.

Kwoh, D.Y. et al.: Transcription-based amplification system and detection of amplified human immunodeficiency virus type 1 with a bead-based sandwich hybridization format, Proc. Natl. Acad. Sci. USA, vol. 86, Feb. 1989, pp. 1173-1177.

Guatelli, John C. et al.: Isothermal, in vitro amplification of nucleic acids by a multienzyme reaction modeled after retroviral replication, Proc. Natl. Acad. Sci. USA, vol. 87, Mar. 1990, pp. 1874-1878.

Braasch, Dwaine A. et al.: Locked nucleic acid (LNA): fine-tuning the recognition of DNA and RNA, Chemistry & Biology, vol. 8, 2001, pp. 1-7.

Wang, J. et al: Determination of Human-Adrenergic Receptor Haplotypes by Denaturation Selective Amplification and Subtractive Genotyping, American Journal of Human Genetics, American Society of Human Genetics, vol. 69, No. 4, Oct. 16, 2001, p. 542.

Jin, Li et al.: Replacing PCR with Cold-PCR enriches variant DNA sequences and redefines the sensitivity of genetic testing, Nature Medicine, vol. 14, No. 5, May 1, 2008, pp. 479-584.

Suspene, Rodolphe et al.: Inversing the natural hydrogen bonding rule to selective amplify GC-rich ADAR-edited RNAs, Nucleic Acids Research, Oxford University Press, GB, vol. 36, No. 12, Jul. 1, 2008, pp. 1-10.

Supplementary European Search Report and Written Opinion dated Jul. 8, 2011.

Mao, H. et al., Synthesis of radioactive single-stranded DNA probes using asymmetrical PCR and oligonucleotide random priming. BioTechniques vol. 27, No. 4, pp. 674-678 (1999).

Volker, Jens et al., High-resolution calorimetric and optical melting profiles of DNA plasmids: Resolving contributions from intrinsic melting domains and specifically designed inserts. Biopolymers, vol. 50, Issue 3, pp. 303-318, Sep. 1999.

Montgomery, Jesse et al., Simultaneous mutations scanning and genotyping by high-resolution DNA melting analysis. Nature Protocols vol. 2, No. 1, pp. 59-66 (2007).

Zhang, Y. et al., An amplification and ligation-based method to scan for unknown mutations in DNA. Hum Mutat. Aug. 2002; 20(2): pp. 139-147.

Zhao, Y. et al., p53 gene mutations in non-small cell lung cancer detected by polymerase chain reactions single-strand conformation polymorphism analysis. Chin Med Sci J., Sep. 1999; vol. 14, No. 3, pp. 134-137.

Huang, C.L. et al., Mutations of p53 and K-ras genes as prognostic factors for non-small cell lung cancer. Int J Oncol. Mar. 1998; vol. 12, No. 3, pp. 553-563.

Pomp, D. et al., Organic solvents as facilitators of polymerase chain reaction. BioTechniques Jan. 1991; vol. 10, No. 1, pp. 58-59.

Wetmur, J.G., DNA probes: applications of the principles of nucleic acid hybridization. Crit Rev Biochem Mol Biol. 1991; 26(3/4), pp. 227-259.

Saiki, R.K. et al., Enzymatic amplifications of beta-globin genomic sequences and restriction site analysis for diagnosis of sickle cell anemia. Science Dec. 20, 1985; vol. 230, No. 4732, pp. 1350-1354.

Rehbein, H. et al., Comparison of different methods to produce single-strand DNA for identification of canned tuna by single-strand conformation polymorphism analysis. Electrophoresis, Jun. 1998; 19(8-9), pp. 1381-1384.

Compton, J., Nucleic acid sequence-based amplification. Nature, vol. 350, pp. 91-92 (Mar. 7, 1991).

Paner, T.M. et al., Analysis of melting transitions of the DNA hairpins formed from the oligomer sequences d[GGATAC (S)4GTATCC] (X=A, T, G. C). Biopolymers, Dec. 1990; vol. 29(14), pp. 1715-1734.

Vamosi, G. et al., The helix-coil transition of DNA duplexes and hairpins observed by multiple fluorescence parameters. Biochemistry, Oct. 6, 1998;37(40), pp. 14300-14316.

Wittwer, C.T. et al., The LightCycler: a microvolume multisample fluorimeter with rapid temperature control. BioTechniques, Jan. 1997; vol. 22, No. 1, pp. 176-181.

Latorra, D. et al., Enhanced allele-specific PCR discrimination in SNP genotyping using 3' locked nucleic acid (LAN) primers. Hum Mutat. Jul. 2003;22(1), pp. 79-85.

Smith, T.F. et al., Comparison of biosequences. Adv. Appl Math, vol. 2 (1981), pp. 482-489.

Lazaro, Conxi et al., Mutation analysis of genetic diseases by asymmetric PCR SSCP and ethidium bromide staining: application to neurofibromatosis and cystic fibrosis. Molecular and Cellular Probes, vol. 6, Issue 5, Oct. 1992, pp. 357-359.

Obika, Satoshi et al., Stability and structural features of the duplexes containing nucleoside analogues with a fixed N-type conformation ,2'-0,4'-c-methyleneriounucleosides. Tetrahedron Letters, vol. 39, Issue 30, Jul. 23, 1998, pp. 5401-5404.

Koshhin, Alexei A. et al., LNA (Locked Nucleic Acids): Synthesis of the adenine, cytosine, guanine, 5-methylcytosine, thymine and uracil bicyclonucleoside monomers, oligomerisation, and unprecedented nucleic acid recognition. Tetrahedron, vol. 54, Issue 14, Apr. 2, 1998, pp. 3607-3630.

Beaucage, S.L. et al., Deoxynucleoside phosphoramidites—A new class of key intermediates for deoxypolynucleotide synthesis. Tetrahedron Letters, vol. 22, Issue 20, 1981, pp. 1859-1863.

U.S. 7,226,739, 06/2007, Wittwer et al. (withdrawn).

"Prognostic significance of K-ras, p53, bcl-2, PCNA, CD34 in radically resected non-small cell lung cancers", F. Grossi et al., European Journal of Cancer, vol. 39, 2003, pp. 1242-1250.

"Prognostic Significance of p53 Alterations in Patients with Non-Small Cell Lung Cancer: A Meta-Analysis 1", T. Mitsudomi et al., Clinical Cancer Research, vol. 6, Oct. 2000, pp. 4055-4063.

"p53 Gene Mutations Are Associated with Shortened Survival in Patients with Advanced Non-small Cell Lung Caner: An Analysis of Medically Managed Patients 1", Isao Murakami et al., Clinical Cancer Research, vol. 6, Feb. 2000, pp. 526-530.

"Specific p53 Mutations Detected in Plasma and Tumors of Hepatocellular Carcinoma Patients by Electrospray Ionization Mass Spectrometry 1", Peta E. Jackson, Cancer Research, vol. 61, Jan. 1, 2001, pp. 33-35.

"p53 Mutation in Plasma DNA and Its Prognostic Value in Breast Cancer Patients 1", Z. M. Shao et al., Clinical Cancer Research, vol. 7, Aug. 2001, pp. 222-2227, retracted Sep. 2002.

"Mutations of p53 gene can be detected in the plasma of patients with large bowel carcinoma", F. Mayall et al., J Clin Pathol, vol. 51, Apr. 29, 1998, pp. 611-613.

"Tumor DNA in Plasma at Diagnosis of Breast Cancer Patients is a Valuable Predictor of Disease-free Survival 1", Jose M. Silva, Clinical Cancer Research, vol. 8, Dec. 2002, pp. 3761-3766.

"Microsatellite alterations and TP53 mutations in plasma DNA of small-cell lung cancer patients: Follow-up study and prognostic significance", R. Gonzalez et al., Annals of Oncology, vol. 11, 2000, pp. 1097-1104.

"Mutations in the Epidermal Growth Factor Receptor and in KRAS are Predictive and Prognostic Indicators in Patients with Non-Small-Cell Lung Cancer Treated with Chemotherapy Alone and in Combination with Erlotinib", David A. Eberhard et al., Journal of Clinical Oncology, vol. 23, No. 25, Sep. 1, 2005.

"Mutations of the Epidermal Growth Factor Receptor Gene in Lung Cancer: Biological and Clinical Implications", Takayuki Kosaka et al., Cancer Research, vol. 64, Dec. 15, 2004, pp. 8919-8923.

"Clinical and Biological Features Associated with Epidermal Growth Factor Receptor Gene Mutations in Lung Cancers", Hisayuki Shigematsu et al., Journal of the National Cancer Institute, vol. 97, No. 5, Mar. 2, 2005, pp. 339-346.

"Patterns of somatic mutation in human cancer genomes", Christopher Greenman et al., Nature, vol. 446, Mar. 8, 2007, pp. 153-158.

"Sensitive Sequencing Method for KRAS Mutation Detection by Pyrosequencing", Shuji Ogino et al., Journal of Molecular Diagnostics, vol. 7, No. 3, Aug. 2005, pp. 413-421.

"Pyrosequencing: History, biochemistry and future", Afshin Ahmadian et al., Clinics Chimica Acta, vol. 363, 2006, pp. 83-94.

"Gene Promoter Methylation in Plasma and Sputum Increases with Lung Cancer Risk", Steven A. Belinsky et al., Clin. Cancer Res, vol. 11, No. 18; Sep. 15, 2005.

"Circulating nucleic acids in plasma/serum", Jason C. H. Tsang et al., Pathology, vol. 293, No. 2, Apr. 2007, pp. 197-207.

"Fetal DNA Analyzed in Plasma from a Mother's Three Consecutive Pregnancies to Detect Paternally Inherited Aneuploidy", Chih-Ping Chen et at., Clinical Chemistry, vol. 47, No. 4, 2001.

Evaluation de la determination du statut Rhesus-D foetal sur plasma maternel par la technique d'hemi-nested PCR (Evaluation of conventional hemi-nested PCR analysis for fetal RHD determination in maternal plasma), D. Dif-Couvreux et al., J Gynecol Obstet Biol Reprod, vol. 35, 2006, pp. 658-664.

"Hypermethylation of RASSF1A in Human and Rhesus Placentas", Rossa W. K. Chiu et al., The American Journal of Pathology, vol. 170, No. 3, Mar. 2007, pp. 941-950.

"Mass Spectrometric Detection of an SNP Panel as an Internal Positive Control for Fetal DNA Analysis in Maternal Plasma", K. C. Chow et al., Clinical Chemistry, vol. 53, No. 1, 2007.

"Diagnostic developments involving cell-free (circulating) nucleic acid", Yu-Kawn Tong et al., Clinica Chimica Acta, vol. 363, 2006, pp. 187-196.

"Thermal denaturation of double-stranded nucleic acids: prediction of temperatures critical for gradient gel electrophoresis and polymerase chain reaction", Gerhard Steger, Nucleic Acids Research, vol. 22, No. 14, 1994, pp. 2760-2768.

"Random Mutagenesis-PCR to Introduce Alterations into Defined DNA Sequences for Validation of SNP and Mutation Detection Methods", Michael L. Nickerson et. al., Human Mutation, vol. 17, 2001, pp. 210-219.

"Thermal stability of DNA", R. D. Blake et al., Nucleic Acids Research, vol. 26, No. 14, 1998, pp. 2232-3332.

\* cited by examiner

FIGURE 1

A PRINCIPLE OF COLD PCR
(Co-amplification at Lower Denaturation temperature)

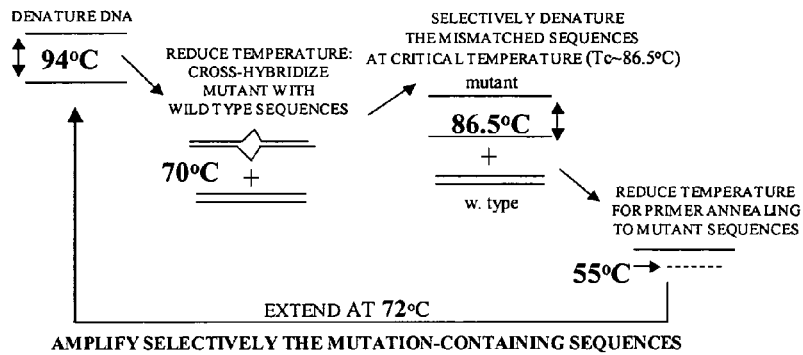

AMPLIFY SELECTIVELY THE MUTATION-CONTAINING SEQUENCES

B COLD-PCR
(simplex, multiplex, or common linker-mediated CO.L.D-PCR)

| MALDI-TOF (Aim 1) | HR-Melting (Aim 2) | Di-deoxy-sequencing | Single-molecule Sequencing (Aim 3) | Pyrosequencing, SSCP, dHPLC, CCM, RFLP, QRT-PCR, etc |

Figure 1. A. Illustration of the enrichment protocol. An example for a 167 bp p53 exon 8 sequence is depicted. The formation of mismatches anywhere along the sequence during PCR enables preferential denaturation and amplification of minor (mutant) alleles at every PCR cycle.. B. Replacement of PCR with the enrichment method: All PCR-based genetic testing assays stand to benefit by mutation-enrichment during the PCR step that precedes them.

PRINCIPLE OF OSCILATING COLD PCR
(an example of a 87 bp p53 exon 8 sequence with Tc=83.5 is shown)

REPEAT THE ENTIRE COURSE FOR SEVERAL CYCLES:
AMPLIFY SELECTIVELY THE MUTATION-CONTAINING SEQUENCES AT EVERY CYCLE

Figure 2: PRINCIPLE OF OSCILATING ENRICHMENT PROTOCOL

Figure 4: Comparison of enrichment PCR with regular-PCR followed by Sanger Di-deoxy-sequencing. Dilutions of DNA from cell lines with p53 mutations into wild-type reveal the mutation enrichment at several sequence positions via the enrichment procedure Figure 5: Comparison of enriched with regular-PCR followed by Sanger Di-deoxy-sequencing. Dilutions of DNA from cell lines with Kras mutations into wild-type reveal the mutation enrichment at several sequence positions via COLD-PCR

Figure 6: Clinical tumor samples with low-prevalence mutations in p53 exon 8: Comparison of enriched v. regular-PCR followed by Sanger Di-deoxy-sequencing. Mutation enrichment enables detection of mutations.

Figure 7: A. Mutations that reduce melting temperature can be enriched in a shortened enrichment protocol: enrichment of several p53 mutations in a 87 bp sequence followed by Sanger sequencing are depicted. B. Amplicons <100 bp result to higher enrichment of mutations. However the mutation enrichment is substantial (10-fold) for at least 200 bp sequences.

```
                        SEQUENCE LISTING

<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcttctcttt tcctatcctg                                              20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cttacctcgc ttagtgct                                                18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tggtaatcta ctgggacg                                                18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cggagattct cttcctct                                                18

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
taactgcacc cttggtc                                                 17

<210> SEQ ID NO 6
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 6
aacttgtggt agttggacct                                                  20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctctattgtt ggatcatatt                                                  20

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caggacaggc acaaaca                                                     17

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aggacaggca caaacac                                                     17

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acagctttga ggtgcgt                                                     17

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgtggtagtt ggacctg                                                     17

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
```

```
    primer

<400> SEQUENCE: 12
actcttgcct acgccac                                                      17

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
tttgaggtgc atgtttgtgc c                                                 21
```

ENRICHMENT OF A TARGET SEQUENCE

RELATED APPLICATION

This application claims the benefit of U.S. Provisional Application No. 60/962,838, filed on Aug. 1, 2007. The entire teachings of the above application is incorporated herein by reference.

BACKGROUND

A commonly encountered situation in genetic analysis entails the need to identify a low percent of variant DNA sequences ('target sequences') in the presence of a large excess of non-variant sequences ('reference sequences'). Examples for such situations include: (a) identification and sequencing of a few mutated alleles in the presence of a large excess of normal alleles; (b) identification of a few methylated alleles in the presence of a large excess of unmethylated alleles (or: vice versa) in epigenetic analysis; (c) identification and genotyping of a few fetal DNA sequences circulating in the blood of the mother where a large excess of mother's DNA sequences are also present; and (d) identification of tumor-circulating DNA in blood of cancer patients (or people suspected of having cancer) in the presence of a large excess of wild-type alleles.

While reliable high throughput screening methods for germline or high-prevalence somatic mutations have recently been described (Thomas, R. K., et al. (2007) Nat Genet, 39, 347-351; Chou, L. S., et al. (2005) Am J Clin Pathol, 124; 330-338; Thomas, R. K., et al. (2006) Nat Med, 12; 852-855) detection of low-prevalence somatic mutations in tumors with heterogeneity, stromal contamination or in bodily fluids is still problematic. And yet, the clinical significance of identifying these mutations is major in several situations. For example: (a) in lung adenocarcinoma, low-level EGFR mutations that cannot be identified by regular sequencing can confer positive response to tyrosine kinase inhibitors (Paez, J. G., et al. (2004) Science, 304; 1497-1500.) or drug resistance (Janne, P. A., et al. (2006) Clin Cancer Res, 12; 751-758) (b) mutations in plasma useful as biomarkers for early detection (Diehl, F., et al. (2005) Proc Natl Acad Sci USA, 102; 16368-16373) or tumor response to treatment (Kimura, T., et al. (2004) Ann N Y Acad Sci, 1022; 55-60) cannot be sequenced using conventional methods; and (c) mutations in tumors with frequent stromal contamination, such as pancreatic or prostate, can be 'masked' by presence of wild-type alleles, thus requiring laborious micro-dissection or missing mutations altogether.

SUMMARY OF THE INVENTION

The present invention is directed to methods, compositions, software and devices for enriching low abundance alleles from a sample. The method is based in part on a modified nucleic acid amplification protocol that includes incubating the reaction mixture at a critical denaturing temperature or "Tc". By employing the present invention the current detection limits of all PCR-based technologies are greatly improved.

The "critical temperature" or "Tc" refers to a temperature below the melting temperature "$T_m$" of the reference sequence. In some embodiments, the Tc is below the $T_m$ of both the reference and target sequence. The critical temperature takes advantage of the lower $T_m$ of the double stranded target sequence or the target-reference cross hybridized double stranded DNA duplex so as to preferentially denature these duplexes over the reference/reference homoduplexes. When the target sequence and reference sequence cross hybridize, minor sequence differences of one or more single nucleotide mismatch anywhere along a short (e.g., <200 bp) double stranded DNA sequence will generate a small but predictable change in the melting temperature ($T_m$) for that sequence (Lipsky, R. H., et al. (2001) Clin Chem, 47, 635-644; Liew, M., et al. (2004) Clin Chem, 50, 1156-1164). Depending on the exact sequence context and position of the mismatch, melting temperature changes of 0.1-20° C., are contemplated.

The critical denaturing temperature (Tc) is the temperature below which PCR efficiency drops abruptly for a reference nucleic acid sequence. For example, a 167 by p53 sequence amplifies well if the PCR denaturing temperature is set at 87° C., amplifies modestly at 86.5° C. and yields no detectable product if PCR denaturation is set at 86° C. or less. Therefore in this example Tc~86.5° C.

In a first aspect, the invention is directed to a method for enriching a target sequence in a nucleic acid sample suspected of having target and reference sequences. The method includes subjecting the amplification reaction mixture to a first denaturing temperature that is above the melting temperature "$T_m$" of a reference sequence. Next, the temperature of the amplification reaction mixture is decreased allowing the single-stranded target sequences and reference sequences to hybridize to form double-stranded molecules. Thus, the reaction includes hybridization homoduplexes of target-target, reference-reference and heteroduplexes of target-reference strands. A heteroduplex by definition is an imperfectly matched duplex which nevertheless contains sufficient homology between strands to maintain a duplex form in the reaction mixture. A homoduplex by definition is a perfectly matched duplex. The temperature of the reaction mixture is then increased to the Tc, resulting in the preferential denaturation of the target-reference sequence hybridization duplexes. The Tc or critical temperature is below the $T_m$ of the reference sequence and can be determined by the methods described herein. At the Tc, the target-reference sequence duplexes (and target-target sequence duplexes only if having a lower $T_m$ than the reference sequence) are substantially denatured, whereas the target-target duplexes (if having a $T_m$ equal to or greater than the $T_m$ of the reference sequence) and the reference-reference sequence duplexes are substantially undenatured. "Substantially" means at least 60%, preferably at least 70%, more preferably at least 80%, even more preferably at least 90% and most preferably at least 98% in a given denatured or undenatured form. After the preferential denaturation of the target-reference duplexes and target-target duplexes (those that have a lower $T_m$ than the reference sequence), a reduced temperature is applied to the reaction mixture so as to allow a pair of primers to anneal to the target sequence. The annealed primers are then extended, thus enriching the target sequence relative to the reference sequence in the sample.

In another aspect, the invention is directed to yet another method of enriching a target sequence. In this method a nucleic acid sample suspected of containing each of a target sequence and a reference sequence is denatured by applying a first denaturing temperature that is above the $T_m$ of the reference sequence. Next, the target and reference strands are annealed to each other so as to form double stranded target-reference sequence duplexes. The target-reference sequence duplex forms and is present in the reaction mixture along with double stranded target-target and reference-reference sequence duplexes. The double stranded target-reference and target-reference sequence duplexes are preferentially denatured by applying the Tc to the sample. At the Tc, the target-reference sequence duplexes (and target-target sequence duplexes only if having a lower $T_m$ than the reference sequence) are substantially denatured, whereas the target-target duplexes (if having a $T_m$ equal to or greater than the $T_m$ of the reference sequence) and the reference-reference sequence duplexes are substantially undenatured. "Substantially" means at least 60%, preferably at least 70%, more preferably at least 80%, even more preferably at least 90% and most preferably at least 98% in a given denatured or undenatured form. A pair of primers are then annealed to the target sequence and are extended, thus increasing the concentration of the target sequence relative to the reference sequence in the sample.

In still another aspect, the invention is directed to a method for enriching a target sequence by performing a nucleic acid amplification reaction protocol. The amplification reaction protocol includes a first denaturing temperature and a second denaturing temperature. The first denaturing temperature is above the $T_m$ of the reference sequence and the second denaturing temperature is below the $T_m$ of the reference sequence.

In another aspect, the invention is directed to a method of enriching a target sequence, which has a lower $T_m$ than the corresponding reference sequence, by subjecting an amplification reaction mixture to a Tc, reducing the temperature of the reaction mixture and extending a primer pair. The amplification reaction mixture is suspected of containing each of a target sequence and a reference sequence. The Tc is below the $T_m$ of the reference sequence, thus allowing for the preferential denaturation of the target sequence with the lower $T_m$. At the Tc, the target-reference sequence duplexes and target-target sequence duplexes are substantially denatured, whereas the reference-reference sequence duplexes are substantially undenatured. "Substantially" means at least 60%, preferably at least 70%, more preferably at least 80%, even more preferably at least 90% and most preferably at least 98% in a given denatured or undenatured form. The step of reducing the temperature of the reaction mixture allows the pair of primers to anneal to the target sequence. These annealed primers are then extended by a polymerase, increasing the amount of the target sequence in the sample relative to the reference sequence.

In still yet another aspect, the invention is directed to a method of enriching a target sequence by subjecting an amplification reaction mixture to multiple cycles of annealing conditions and the Tc. The amplification reaction mixture, suspected of having each of a target and reference sequence, is first subjected to a first denaturing temperature which is above the $T_m$ of the reference sequence. Next, the sample is cycled between two different temperature incubation steps. In the first incubation step, the temperature is decreased so as to allow the hybridization of the target sequence with the reference sequence so as to form a duplex. In the second incubation step, the temperature is increased to the Tc, which is below the $T_m$ of the reference sequence. At the Tc, the target-reference sequence duplexes (and target-target sequence duplexes only if having a lower $T_m$ than the reference sequence) are substantially denatured, whereas the target-target duplexes (if having a $T_m$ equal to or greater than the $T_m$ of the reference sequence) and the reference-reference sequence duplexes are substantially undenatured. "Substantially" means at least 60%, preferably at least 70%, more preferably at least 80%, even more preferably at least 90% and most preferably at least 98% in a given denatured or undenatured form. These first and second steps are then repeated one or more times. Once the cyclic incubation step is complete, the temperature of the reaction mixture is decreased so as to allow a primer pair to anneal to the target sequence. These primers are then extended by a polymerase, thus enriching the target sequence relative to the reference sequence in the sample.

BRIEF DESCRIPTION OF THE DRAWINGS

FIG. 1 illustrates one embodiment of the target sequence enrichment procedure of the invention utilizing a first denaturing temperature and the Tc.

DETAILED DESCRIPTION

Figure 2:
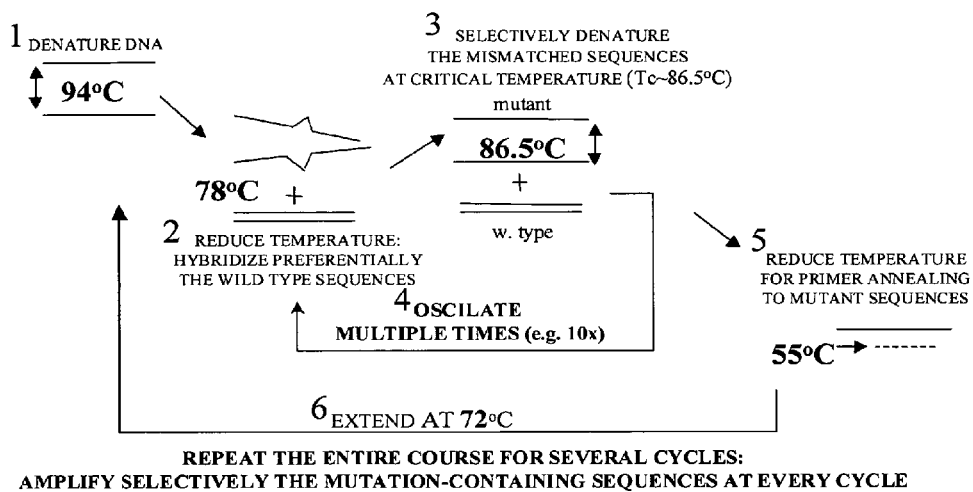
FIG. 2 illustrate one embodiment of the target sequence enrichment procedure of the invention utilizing an oscillating annealing/Tc step.

The present invention is directed to methods, compositions, software and devices for enriching low abundance alleles (e.g., target sequences) from a sample. The present invention is directed, in part, on the selective enrichment of target sequences by applying a critical denaturing temperature to a reaction mixture. The critical denaturing temperature or Tc is a temperature below the melting temperature $T_m$ of the reference sequence. The critical temperature takes advantage of the lower $T_m$ of the double stranded target sequence or the target-reference cross hybridized double stranded DNA duplex so as to preferentially denature these duplexes over the reference/reference homoduplexes.

Many known mutation detection methods stand to benefit from the present invention which employs an amplification protocol which selectively enriches the target sequence. The use of PCR as the initial step for genetic testing is used in most mutation and sequencing reactions. Generally, a nucleic acid sequence (e.g., genomic DNA/cDNA) is amplified as a first step, followed by di-deoxy-sequencing or a mutation screening method (e.g. SSCP, dHPLC, MALDI-TOF, pyrosequencing, High Resolution Melting. Accordingly, the limits of essentially all mutation detection methods would uniformly benefit if enrichment of mutation-containing sequences (e.g., target sequences) was performed during the PCR step that precedes screening.

DEFINITIONS

As used herein, the term "enriching a target sequence" refers to increasing the amount of a target sequence and increasing the ratio of target sequence relative to the corresponding reference sequence in a sample. For example, where the ratio of target sequence to reference sequence is initially 5% to 95% in a sample, the target sequence may be preferentially amplified in an amplification reaction so as to produce a ratio of 70% target sequence to 30% reference sequence. Thus, there is a 14 fold enrichment of the target sequence relative to the reference sequence. Enrichment of a target sequence results in a 2× to 200× increase in the target sequence relative to the reference sequence prior to enrichment. The enrichment of the target is at least a 2×, 3×, 4×, 5×, 6×, 7×, 8×, 9×, 10×, 15×, 20×, 25×, 30×, 35×, 40×, 45×, 50×, 60×, 70×, 80×, 90× 100×, 150×, 200× or more fold enrichment over the reference sequence. Enrichment of a target sequence results in a sample having 10%, 15%, 20%, 25%, 30%, 35%, 40%, 45%, 50%, 55%, 60%, 65%, 70%, 80%, 90%, 95% or more, target sequence compared to reference sequence (e.g., 10% target sequence: 90% reference sequence to 95% target sequence: 5% reference sequence).

As used herein the term "target sequence" refers to a nucleic acid that is less prevalent in a nucleic acid sample than a corresponding reference sequence. The target sequence makes-up less than 50% of the total amount of reference sequence+target sequence in a sample. Preferably the target sequence is expressed at the RNA and/or DNA level 1:10, 1:15, 1:20, 1:25×, 1:30, 1:35, 1:40, 1:45, 1:50, 1:60, 1:70, 1:80, 1:90, 1:100, 1:150, 1:200× or less than the reference sequence. In one embodiment, the target sequence is a mutant allele. For example, a sample (e.g., blood sample) may contain numerous normal cells and few cancerous cells. The normal cells contain non-mutant or wild-type alleles, while the small number of cancerous cells contains somatic mutations. In this case the mutant is the target sequence while the wild-type sequence is the reference sequence. In another embodiment, the invention is directed to detecting fetal DNA in a nucleic acid sample obtained from a mother. In this embodiment, the target sequence is present in the fetal DNA while the more prevalent mother DNA contains the reference sequence. As used herein, a target sequence is meant to include fetal DNA obtained from a pregnant mother. As used herein, a "target strand" refers to a single nucleic acid strand of a target sequence.

The target sequence is about 17-2000 nucleotides long. In one embodiment the target sequence is 20, 30, 40, 50, 60, 70, 80, 90, 100, 110, 120, 130, 140, 150, 160, 170, 180, 190, 200, 250, 300, 350, 400, 450, 500, 600, 700, 800, 900 or more nucleotides long. Target sequences share at least 50%, 60%, 70%, 80%, 85%, 90%, 91%, 92%, 93%, 94%, 95%, 96%, 97%, 98%, 99% or more homology to the corresponding reference sequence, but differs by at least one nucleotide from the reference sequence. Target sequences according to the invention can be amplified via PCR with the same pair of primers as those used for the reference sequence.

As used herein, the term "reference sequence" refers to a nucleic acid that is more prevalent in a nucleic acid sample than a corresponding target sequence (e.g, same gene but different nucleic acid sequence). The reference sequence makes-up over 50% of the total reference sequence+target sequence in a sample. Preferably the reference sequence is expressed at the RNA and/or DNA level 10×, 15×, 20×, 25×, 30×, 35×, 40×, 45×, 50×, 60×, 70×, 80×, 90× 100×, 150×, 200× or more than the target sequence. In one embodiment, the reference sequence is a wild-type allele. For example, a sample (e.g., blood sample) may contain numerous normal cells and few cancerous cells. The normal cells contain non-mutant or wild-type alleles, while the small number of cancerous cells contain somatic mutations. In this case the wild-type sequence is the reference sequence while the mutant sequence is the target sequence (e.g., mutant allele). As used herein, a "reference strand" refers to a single nucleic acid strand of a reference sequence.

The reference sequence is about 17-2000 nucleotides long. In one embodiment the reference sequence is 20, 30, 40, 50, 60, 70, 80, 90, 100, 110, 120, 130, 140, 150, 160, 170, 180, 190, 200, 250, 300, 350, 400, 450, 500, 600, 700, 800, 900 or more nucleotides long. Reference sequences will share at least 50%, 60%, 70%, 80%, 85%, 90%, 91%, 92%, 93%, 94%, 95%, 96%, 97%, 98%, 99% or more homology to the corresponding target sequence, but will differ by at least one nucleotide from the target sequence. Reference sequences according to the invention can be amplified by PCR with the same pair of primers as that used for the reference sequence.

The term "allele" refers to alternative forms of a gene, portion thereof or non coding region of DNA that occupy the same locus or position on homologous chromosomes that have at least one difference in the nucleotide sequence. The term allele can be used to describe DNA from any organism including but not limited to bacteria, viruses, fungi, protozoa, molds, yeasts, plants, humans, non-humans, animals, and archaebacteria. The alleles may be found in a single cell (e.g., two alleles, one inherited from the father and one from the mother) or within a population of cells (e.g., a wild-type allele from normal tissue and a somatic mutant allele from diseased tissue).

An allele can be 17-2000 nucleotides long. In one embodiment the allele is 20, 30, 40, 50, 60, 70, 80, 90, 100, 110, 120, 130, 140, 150, 160, 170, 180, 190, 200, 250, 300, 350, 400, 450, 500, 600, 700, 800, 900 or more nucleotides long. Alleles will generally share 50%, 60%, 70%, 80%, 85%, 90%, 91%, 92%, 93%, 94%, 95%, 96%, 97%, 98%, 99% or more homology to each other. Alleles according to the invention can be amplified by PCR with the same pair of primers.

In one embodiment, the present invention is used to enrich a polymorphism. Any given gene may have none, one, or many allelic forms (polymorphism). Common mutational changes which give rise to alleles may be the result of natural or artificial (e.g., chemical carcinogens) deletions, additions, or substitutions of nucleotides. Each of these types of changes may occur alone, or in combination with the others, one or more times in a given sequence.

Several different types of polymorphisms have been reported. A restriction fragment length polymorphism (RFLP) is a variation in DNA sequence that alters the length of a restriction fragment (Botstein et al., *Am. J. Hum. Genet.* 32:314-331 (1980)). The restriction fragment length polymorphism may create or delete a restriction site, thus changing the length of the restriction fragment. RFLPs have been widely used in human and animal genetic analyses (see WO 90/13668; WO 90/11369; Donis-Keller, *Cell* 51:319-337 (1987); Lander et al., *Genetics* 121:85-99 (1989)). When a heritable trait can be linked to a particular RFLP, the presence of the RFLP in an individual can be used to predict the likelihood that the individual will also exhibit the trait. RFLP can be used in combination with the enrichment methods described herein so as to enhance the detection of polymorphisms. Such methods are described herein in Example 9.

Other polymorphisms take the form of short tandem repeats (STRs) that include tandem di-, tri- and tetra-nucleotide repeated motifs. These tandem repeats are also referred to as variable number tandem repeat (VNTR) polymorphisms. VNTRs have been used in identity and paternity analysis (U.S. Pat. No. 5,075,217; Armour et al., *FEBS Lett.* 307:113-115 (1992); Horn et al., WO 91/14003; Jeffreys, EP 370,719), and in a large number of genetic mapping studies.

Other polymorphisms take the form of single nucleotide variations between individuals of the same species. Such polymorphisms are far more frequent than RFLPs, STRs (short tandem repeats) and VNTRs (variable number tandem repeats). Some single nucleotide polymorphisms occur in protein-coding sequences, in which case, one of the polymorphic forms may give rise to the expression of a defective or other variant protein and, potentially, a genetic disease. Other single nucleotide polymorphisms occur in noncoding regions. Some of these polymorphisms may also result in defective protein expression (e.g., as a result of defective splicing). Other single nucleotide polymorphisms have no phenotypic effects.

Yet other mutations include somatic mutations. Somatic mutations are alterations in DNA that occurs after conception. Somatic mutations can occur in any of the cells of the body except the germ cells (sperm and egg) and therefore are not passed on to children. These alterations can (but do not always) lead to cancer or other diseases.

As used herein, the term "wild-type" refers to the most common polynucleotide sequence or allele for a certain gene in a population. Generally, the wild-type allele will be obtained from normal cells.

As used herein, the term "mutant" refers to a nucleotide change (i.e., a single or multiple nucleotide substitution, deletion, or insertion) in a nucleic acid sequence. A nucleic acid which bears a mutation has a nucleic acid sequence (mutant allele) that is different in sequence from that of the corresponding wild-type polynucleotide sequence. The methods of the invention are especially useful in selectively enriching a mutant allele which contains between 1 and 500 nucleotide sequence changes. A mutant allele may have 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400 or 500 nucleotide sequence changes compared to a corresponding wild-type allele. Preferably, a mutation in a mutant allele will contain between 1 and 10 nucleotide sequence changes, and more preferably between 1 and 5 nucleotide sequence changes. The mutant allele will have 50%, 60%. 70%, 80%, 85%, 90%, 91%, 92%, 93%, 94%, 95%, 96%, 97%, 98%, 99% or more homology to the wild-type allele. Generally, the mutant allele will be obtained from diseased tissues or cells and is associated with a disease state.

As used herein the term "melting temperature" or "$T_m$" refers to the temperature at which a polynucleotide dissociates from its complementary sequence. Generally, the $T_m$ may be defined as the temperature at which one-half of the Watson-Crick base pairs in a duplex nucleic acid molecule are broken or dissociated (i.e., are "melted") while the other half of the Watson-Crick base pairs remain intact in a double stranded conformation. In other words the $T_m$ is defined as the temperature at which 50% of the nucleotides of two complementary sequences are annealed (double strands) and 50% of the nucleotides are denatured (single strands). $T_m$, therefore defines a midpoint in the transition from double-stranded to single-stranded nucleic acid molecules (or, conversely, in the transition from single-stranded to double-stranded nucleic acid molecules).

The $T_m$ can be estimated by a number of methods, for example by a nearest-neighbor calculation as per Wetmur 1991 (Wetmur, J. G. 1991. DNA probes: applications of the principles of nucleic acid hybridization. *Crit. Rev Biochem Mol Biol* 26: 227-259, hereby incorporated by reference) and by commercial programs including Oligo™ Primer Design and programs available on the internet. Alternatively, the $T_m$ can be determined though actual experimentation. For example, double-stranded DNA binding or intercalating dyes, such as ethidium bromide or SYBR-green (Molecular Probes) can be used in a melting curve assay to determine the actual $T_m$ of the nucleic acid. Additional methods for determining the $T_m$ of a nucleic acid are well know in the art and described herein.

As used herein, the term "critical temperature" or "Tc" refers to a temperature below the $T_m$ of the reference sequence. The Tc is applied to preferentially denature the double-stranded target sequence duplex or target sequence/reference sequence double-stranded duplex so as to allow the selective enrichment of the target sequence during an amplification reaction. The critical denaturing temperature (Tc) is the temperature below which PCR efficiency drops abruptly for a given nucleic acid sequence. For example, a 167 by p53 sequence amplifies well if the PCR denaturing temperature is set at 87° C., amplifies modestly at 86.5° C. and yields no detectable product if PCR denaturation is set at 86° C. or less. Therefore in this example Tc~86.5° C. The Tc is about 0.1-20° C. below the $T_m$ of the reference sequence. More preferably the Tc is about 0.1-10° C., 0.1-9° C., 0.1-8° C., 0.1-7° C. 0.1-6° C., 0.2° C.-5° C., 0.3° C.-4.5° C., 0.4-4° C., 0.5-3.5° C., 0.5-3° C., 0.5-3° C., 0.5-2.5° C., 0.5-2° C., 0.5-1.5° C., 0.5-1° C. below the $T_m$ of the reference sequence. In some embodiments, the Tc is below the $T_m$ of both the reference and target sequences. For example, the Tc may be about 0.1-10° C., 0.1-9° C., 0.1-8° C., 0.1-7° C. 0.1-6° C., 0.2° C.-5° C., 0.3° C.-4.5° C., 0.4-4° C., 0.5-3.5° C., 0.5-3° C., 0.5-3° C., 0.5-2.5° C., 0.5-2° C., 0.5-1.5° C., 0.5-1° C. below the $T_m$ of the target sequence.

As used herein, the term "selective denaturation" or "preferential denaturation" refers to the preferential breaking of hydrogen bonds between base pairs in a double-stranded nucleic acid molecule of a target sequence or target/reference sequence duplex to produce in single-stranded target sequence. The selective denaturation of the target sequence is accomplished by applying the critical temperature to the sample containing the target and reference sequences.

As used herein, "primer pair" refers to two primers that anneal to opposite strands of a target and reference sequence so as to form an amplification product during a PCR reaction. The primer pair is designed so as to have a $T_m$ lower than the Tc of the reaction.

As used herein the term "cross-hybridization" refers to a double-stranded duplex formed between two nucleic acid sequences, that differ by one or more nucleotides, by virtue of the formation of hydrogen binds between complementary G and C bases and between complementary A and T or A and U bases. The two complementary nucleic acid sequences hydrogen bond in an antiparallel configuration. In a preferred embodiment, the two nucleic acid sequences are a target sequence and a reference sequence. The cross-hybridized DNA will contain mismatches at the positions of difference between the reference and target sequences. The mismatches can include polymorphisms, mutations, insertions, deletions and other changes that result in such differences. For example, methylation. For example, loops and/or single stranded regions of one or more nucleotides occur at sites of deletions/insertions.

Cross hybridization typically involves denaturing the target and reference sequences, for example by heating, followed by renaturing under conditions (such as temperature) which allow hybridization and duplex formation to occur.

As used herein, a "reaction mixture" is a mixture suspected of containing a target sequence duplex that comprises a suitable buffer for allowing the denaturing of a target sequence.

As used herein, "identity" or "homology" refers to the subunit sequence similarity between two polymeric molecules, e.g., two polynucleotides or two polypeptides. When a subunit position in both of the two molecules is occupied by the same monomeric subunit, e.g., if a position in each of two peptides is occupied by serine, then they are identical at that position. The identity between two sequences is a direct function of the number of matching or identical positions, e.g., if half (e.g., 5 positions in a polymer 10 subunits in length), of the positions in two peptide or compound sequences are identical, then the two sequences are 50% identical; if 90% of the positions, e.g., 9 of 10 are matched, the two sequences share 90% sequence identity.

Percent nucleotide identity can be determined by the default parameters of BLAST. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The comparison window includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

An example of an algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=-4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=-4, and a comparison of both strands.

The BLAST algorithm also performs a statistical analysis of the similarity between two sequences (see, e.g., Karlin & Altschul, *Proc. Nat'l Acad. Sci. USA* 90:58735787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

In a first aspect, the invention is directed to a method for enriching a target sequence in a nucleic acid sample suspected of having target and reference sequences. The reference and target sequences may be amplified prior to use in the present method. That is the reference and target sequences of interest may be amplified from a genomic template in a PCR reaction prior to use in the present method. An aliquot from this PCR reaction is then transferred for use in the selective enrichment method. Alternatively, the reference and target sequences need not be subjected to a first PCR reaction but can be used in their native form (e.g., genomic DNA) in the selective enrichment method. The target and reference sequences can be obtained from any nucleic acid sequence including, genomic DNA, cDNA, viral DNA, mammalian DNA, fetal DNA or bacterial DNA. While the reference sequence is generally the wild-type allele and the target sequence is the mutant allele, the reverse may also be true. The mutant allele may include any one or more nucleotide deletions, insertions or alterations. In some embodiments, the mutant allele is a somatic mutation. In other embodiments, the target sequence is methylated DNA while the reference sequence is un-methylated DNA. Alternatively, the target sequence is un-methylated DNA while the reference sequence is methylated DNA. The primers used in the present method are generally design so as to produce reference and target sequence amplification products of about 17 to 1000 bases, more preferably about 25 to 500 bases, and most preferably about 50 to 100 bases in size.

The method includes subjecting the amplification reaction mixture to a first denaturing temperature that is above the melting temperature "$T_m$" of a reference sequence. The $T_m$ of a nucleic acid can be determined through experimentation or estimated by calculation. The skilled artisan is well aware of numerous well known methods for determining the $T_m$ of a nucleic acid, some of which are described herein. The first denaturing temperature is set according to standard procedures used in PCR. Thus, the first denaturing temperature should be sufficiently high so as to allow the full denaturation of the target and reference sequences (e.g., 96° C.). In one embodiment, the first denaturing temperature is about 1° C. to 30° C. above the $T_m$ of the reference sequence, more preferably the $T_m$ of the reference sequence is about 5° C. to 20° C. above the Tm of the reference sequence.

Next, the temperature of the amplification reaction mixture is decreased allowing the target sequences and reference sequences to hybridize. In a preferred embodiment, this hybridization temperature or intermediate temperature (the temperature being below the first denaturing temperature and Tc but above the primer annealing/extension temperature, e.g., about 60° C. to 80° C.) is above the $T_m$ of the primer pair, and thus allows the target and reference sequences to hybridize while preventing binding of the primer pair to the target and/or reference sequences. This annealing step results in the formation of hybridization duplexes of double stranded target-target, reference-reference and target-reference sequences The target-reference hybridization duplexes are then preferentially denatured by increasing the temperature of the reaction mixture to the Tc. The Tc or critical temperature is below the $T_m$ of the reference sequence and can be determined by the methods described herein. In one embodiment, the Tc is about 0.3° C.-5° C. below and more preferably about 0.5° C. to 1.5° C. below the $T_m$ of the reference sequence. Generally, the Tc will be about 70-90° C. The target-target hybridization duplexes may also be preferentially denatured if the target sequence has a nucleotide sequence which results in a lower $T_m$ compared to the reference sequence. At the Tc, the target-reference sequence duplexes (and target-target sequence duplexes only if having a lower $T_m$ than the reference sequence) are substantially denatured, whereas the target-target duplexes (if having a $T_m$ equal to or greater than the $T_m$ of the reference sequence) and the reference-reference sequence duplexes are substantially undenatured. "Substantially" means at least 60%, preferably at least 70%, more preferably at least 80%, even more preferably at least 90% and most preferably at least 98% in a given denatured or undenatured form. The Tc is generally applied from about 1 second to 5 minutes, more preferably 2 seconds to 1 minute and most preferably 5 seconds to 30 seconds.

After the preferential denaturation of the target-reference and/or target-target sequence hybridization duplexes, the temperature of the reaction mixture is reduced so as to allow a primer pair to anneal to the target sequence. The annealed primers are then extended by a nucleic acid polymerase, thus enriching the target sequence relative to the reference sequence in the sample.

The steps of the method are generally repeated for multiple cycles in order to get sufficient amplification of the target and reference sequences. In one embodiment, the steps of the method are repeated for 5-40 cycles and more preferably 10-30 cycles. The optimal number of cycles can be determined by one of ordinary skill in the art. Preferably, the present methods are performed in a PCR device, more preferably under real-time reaction conditions in a real-time detection PCR device, such as the SMARTCYCLER real-time PCR device (Cepheid, Sunnyvale, Calif.) and the Mx3005P real-time PCR device (Stratagene, La Jolla, Calif.). In this embodiment, the reaction mixture may include a nucleic acid detection agent (e.g., nucleic acid detection dye such as SYBR Green dye or LC-Green dye or a probe operatively coupled to a fluorescent dye) for quantifying and/or monitoring the amplification products of the reaction. Once the enrichment of the target sequence is complete the sample may be further processed (e.g., for identification of any genetic alterations enriched by the method, e.g., subjected to a sequencing reaction). The enriched reference sequences may be further processed by a variety of procedures including: MALDI-TOF, HR-Melting, Di-deoxy-sequencing, Single-molecule sequencing, pyrosequencing, RFLP, digital PCR and quantitative-PCR.

In still another aspect, the invention is directed to a method for enriching a target sequence by performing a nucleic acid amplification reaction protocol. The amplification reaction protocol includes a first denaturing temperature and a second denaturing temperature. The first denaturing temperature is above the $T_m$ of the reference sequence and the second denaturing temperature is below the $T_m$ of the reference sequence. The method includes subjecting the amplification reaction mixture to a first denaturing temperature that is above the melting temperature "$T_m$" of a reference sequence. The $T_m$ of a nucleic acid can be determined through experimentation or estimated by calculation. The skilled artisan is well aware of numerous well known methods for determining the $T_m$ of a nucleic acid. The first denaturing temperature is generally selected as one would generally select the denaturing temperature of a PCR reaction and should be sufficiently high so as to allow the denaturing of the target and reference sequences. In one embodiment, the first denaturing temperature is about 1° C. to 30° C. above the $T_m$ of the reference sequence, more preferably the $T_m$ of the reference sequence is about 5° C. to 20° C. above the $T_m$ of the reference sequence.

The second denaturing temperature is below the $T_m$ of the reference sequence and can be determined by the methods described herein. In one embodiment, the Tc is about 0.3° C.-5° C. below the $T_m$ of the reference sequence and more preferably about 0.5° C. to 1.5° C. below the $T_m$ of the reference sequence. Generally, the Tc will be about 70-90° C. The second denaturing temperature is generally applied from about 1 second to 5 minutes, more preferably 2 seconds to 1 minute and most preferably 5 seconds to 30 seconds.

In another aspect, the invention is directed to a method of enriching a target sequence by subjecting an amplification reaction mixture to a Tc, reducing the temperature of the reaction mixture and extending a primer pair. The amplification reaction mixture is suspected of containing a target and a reference sequence. In this aspect, the target sequence has a $T_m$ below the $T_m$ of the reference sequence. The Tc is below the $T_m$ of the reference sequence, thus allowing for the preferential denaturation of the target sequence which has a lower $T_m$ than the reference sequence as a result of its nucleotide composition (e.g., deletion). As with respect to the other aspects of the invention, the reference and target sequences may be amplified prior to use in the present method. That is the reference and target sequences of interest may be amplified from a genomic template in a PCR reaction prior to use in the present method. An aliquot from this PCR reaction is then transferred for use in the selective enrichment method. Alternatively, the reference and target sequences need not be subjected to a first PCR reaction but can be used in their native form in the selective enrichment method, e.g., genomic DNA. The target and reference sequences can be obtained from any nucleic acid sequence including, genomic DNA, cDNA, viral DNA, mammalian DNA, fetal DNA or bacterial DNA. While the reference sequence is generally the wild-type allele and the target sequence is the mutant allele, the reverse may also be true. The mutant allele may include any one or more nucleotide deletions, insertions or alterations. In some embodiments, the mutant allele is a somatic mutation. The primers used in the present method are generally designed so as to produce reference and target sequence amplification products of about 15 to 1000 bases, more preferably about 25 to 500 bases, and most preferably about 50 to 100 bases in size.

The target-target hybridization duplexes are preferentially denatured by increasing the temperature of the reaction mixture to the Tc. The Tc or critical temperature is below the $T_m$ of the reference sequence and can be determined by the methods described herein. In one embodiment, the Tc is about 0.3° C.-5° C. below the $T_m$ of the reference sequence and more preferably about 0.5° C. to 1.5° C. below the $T_m$ of the reference sequence. Generally, the Tc will be about 70-90. The Tc is generally applied from about 1 second to 5 minutes, more preferably 2 seconds to 1 minute and most preferably 5 seconds to 30 seconds. At the Tc, the target-reference sequence duplexes and target-target sequence duplexes are substantially denatured, whereas the reference-reference sequence duplexes are substantially undenatured. "Substantially" means at least 60%, preferably at least 70%, more preferably at least 80%, even more preferably at least 90% and most preferably at least 98% in a given denatured or undenatured form.

The step of reducing the temperature of the reaction mixture allows the primer pair to anneal to the target sequence. These annealed primers are then extended by a polymerase, increasing the amount of the target sequence in the sample. The steps of the method are generally repeated for multiple cycles in order to get sufficient amplification of the target and reference sequences. In one embodiment, the steps of the method are repeated for 5-40 cycles and more preferably 10-30 cycles. The optimal number of cycles can be determined by one of ordinary skill in the art. Preferably, the present methods are performed in a PCR device, more preferably under real-time reaction conditions in a real-time detection PCR device, such as the SMARTCYCLER real-time PCR device (Cepheid, Sunnyvale, Calif.) and the Mx3005P real-time PCR device (Stratagene, La Jolla, Calif.). In this embodiment, the reaction mixture may include a nucleic acid detection agent (e.g., nucleic acid detection dye such as SYBR Green dye or LC-Green dye or a probe operatively coupled to a fluorescent dye) for quantifying and/or monitoring the amplification products of the reaction. Once the enrichment of the target sequence is complete the sample may be further processed, e.g., subjected to a sequencing reaction. The enriched alleles may be further processed by a variety of procedures including: MALDI-TOF, HR-Melting, Di-deoxy-sequencing, Single-molecule sequencing, pyrosequencing, RFLP, digital PCR and quantitative-PCR.

In still yet another aspect, the invention is directed to a method of enriching a target sequence by subjecting an amplification reaction mixture to alternating steps of annealing conditions and denaturing conditions by applying the Tc. The amplification reaction mixture, having a target and reference sequence, is first subjected to a first denaturing temperature which is above the $T_m$ of the reference sequence. As in the other aspects, the reference and target sequences may be amplified prior to use in the present method. That is the reference and target sequences of interest may be amplified from a genomic template in a PCR reaction prior to use in the present method. An aliquot from this PCR reaction is then transferred for use in the selective enrichment method. Alternatively, the reference and target sequences need not be subjected to a first PCR reaction but can be used in their native form in the selective enrichment method, e.g., genomic DNA. The target and reference sequences can be obtained from any nucleic acid sequence including, genomic DNA, cDNA, viral DNA, mammalian DNA, fetal DNA or bacterial DNA. While the reference sequence is generally the allele and the target sequence is the mutant allele, the reverse may also be true. The mutant allele may include any one or more nucleotide deletions, insertions or alterations. In some embodiments, the mutant allele is a somatic mutation. In other embodiments, the target sequence is methylated DNA while the reference sequence is un-methylated DNA. Alternatively, the target sequence is un-methylated DNA while the reference sequence is methylated DNA. The primers used in the present method are generally design so as to produce reference and target sequence amplification products of about 15 to 1000 bases, more preferably about 25 to 500 bases, and most preferably about 50 to 100 bases in size.

The $T_m$ of a nucleic acid can be determined through experimentation or estimated by calculation. The skilled artisan is well aware of numerous well known methods for determining the $T_m$ of a nucleic acid. The first denaturing temperature is generally selected as one would generally select the denaturing temperature of a PCR reaction and should be sufficiently high so as to allow denaturing of the target and reference sequences. In one embodiment, the first denaturing temperature is about 1° C. to 30° C. above the $T_m$ of the reference sequence, more preferably the $T_m$ of the reference sequence is about 5° C. to 20° C. above the $T_m$ of the reference sequence.

Next, the sample is cycled between two different temperature incubation steps. In the first incubation step, the temperature is decreased so as to allow the hybridization of the target sequence with the reference sequence. In the second incubation step, the temperature is increased to the Tc, which is below the $T_m$ of the reference sequence. These first and second steps are then repeated one or more times, more preferably 3-20 times and most preferably 5-10 times.

The first incubation step results in the formation of hybridization duplexes of target-target, reference-reference and target-reference sequences. In a preferred embodiment, this hybridization temperature or intermediate temperature (the temperature being below the first denaturing temperature and Tc but above the primer annealing/extension temperature, e.g., about 60° C. to 80° C.) is above the $T_m$ of the primer pair, and thus allows the target and reference sequences to hybridize while preventing binding of the primer pair to the target and/or reference sequences. The target-reference and target-target (as long as the target has a lower $T_m$ than the reference sequence) hybridization duplexes are then preferentially denatured by increasing the temperature of the reaction mixture to the Tc in the second incubation step. The Tc or critical temperature is below the $T_m$ of the reference sequence and can be determined by the methods described herein. In one embodiment, the Tc is about 0.3° C.-5° C. below the $T_m$ of the reference sequence and more preferably about 0.5° C. to 1.5° C. below the $T_m$ of the reference sequence. Generally, the Tc will be about 70-90° C. The target-target hybridization duplexes are also preferentially denatured if the target sequence has a nucleotide sequence which results in a lower $T_m$ compared to the reference sequence. The Tc is generally applied from about 1 second to 5 minutes, more preferably 2 seconds to 1 minute and most preferably 5 seconds to 30 seconds. Once the cyclic incubation step is complete, the temperature of the reaction mixture is decreased so as to allow the one or more primers to anneal to the target sequence. These primers are then extended by a polymerase, thus enriching the target sequence.

Once each step is competed the reaction may be repeated for multiple cycles in order to get sufficient amplification of the target and reference sequences. In one embodiment, the steps of the method are repeated for 5-40 cycles and more preferably 10-30 cycles. The optimal number of cycles can be determined by one of ordinary skill in the art. Preferably, the present methods are performed in a PCR device, more preferably under real-time reaction conditions in a real-time detection PCR device, such as the SMARTCYCLER real-time PCR device (Cepheid, Sunnyvale, Calif.) and the Mx3005P real-time PCR device (Stratagene, La Jolla, Calif.). In this embodiment, the reaction mixture may include a nucleic acid detection agent (e.g., nucleic acid detection dye such as SYBR Green dye or LC-Green dye or a probe operatively coupled to a fluorescent dye) for quantifying and/or monitoring the amplification products of the reaction. Once the enrichment of the target sequence is complete the sample is subjected to further processing. Further processing includes MALDI-TOF, HR-Melting, Di-deoxy-sequencing, Single-molecule sequencing, pyrosequencing, RFLP, digital PCR and quantitative-PCR.

In another embodiment, the method of the present invention can be used to detect whether methylation has occurred in a target sequence or reference sequence. In a further embodiment, the method utilizes genomic DNA to assay the methylation.

The methylation detection method comprises a chemical or enzymatic approach for methylation-sensitive treatment of DNA. Chemical treatments include the incubation of DNA with sodium bisulfite, which selectively converts non-methylated cytosines to uracils. The DNA is first heat-denatured and then can be treated with 5M bisulfite, pH 5-7. Pretreatment of genomic DNA to remove pre-existing uracils is used prior to bisulfite treatment. This pretreatment consists of uracil glycosylase treatment in the presence of 5 mM hydroxylamine, pH 7. The modified DNA may now be used in the methods of the invention.

Because the methylated cytosines of the reference or target sequence are converted to uracils, they will now form mismatches when duplexed with the opposite strand (target or reference), which was not methylated, during they cross-hybridization step of the reaction.

In yet another aspect, any of the methods of the invention are used to enrich multiple different target sequences in a multi-plex reaction. In this embodiment, the method includes additional sets of primer pairs to the additional target sequences.

In another aspect, the invention is directed to a computer readable medium having program instructions for performing any of the methods of the invention. In a further aspect, the invention is directed to a PCR system for enriching the target sequence. The system includes memory for implementing the program instructions of the computer readable medium.

FIGS. 1 and 2 illustrate two different aspects of the invention. FIG. 1 illustrates an aspect of the invention in which the method utilizes an amplification reaction having a first denaturing temperature and a critical denaturing temperature or Tc. FIG. 2 also illustrates an amplification reaction having a first denaturing temperate and a Tc but further includes oscillating, or repeating, the annealing and critical denaturing temperature step multiple times prior to the primer annealing and extension phase of the reaction.

FIG. 1 shows the procedure for enriching a target sequence in a nucleic acid sample having target and reference sequences. The target and reference sequences can be obtained from any nucleic acid sequence including, genomic DNA, cDNA, viral DNA, mammalian DNA, fetal DNA or bacterial DNA. While the reference sequence is generally the allele and the target sequence is the mutant allele, the reverse may also be true. The mutant allele may include any one or more nucleotide deletions, insertions or alterations. In some embodiments, the mutant allele is a somatic mutation. In other embodiments, the target sequence is methylated DNA while the reference sequence is un-methylated DNA. Alternatively, the target sequence is un-methylated DNA while the reference sequence is methylated DNA.

The method includes subjecting the amplification reaction mixture to a first denaturing temperature (FIG. 1A) that is above the melting temperature "$T_m$" of a reference sequence. The $T_m$ of a nucleic acid can be determined through experimentation or estimated by calculation. The skilled artisan is well aware of numerous well known methods for determining the $T_m$ of a nucleic acid some of which are described herein. The first denaturing temperature is generally selected as one would generally select the denaturing temperature of a PCR reaction and should be sufficiently high so as to allow the full denaturing of the target and reference sequences (e.g., 94° C.). In one embodiment, the first denaturing temperature is about 1° C. to 30° C. above the $T_m$ of the reference sequence, more preferably the $T_m$ of the reference sequence is about 5° C. to 20° C. above the $T_m$ of the reference sequence.

Next, the temperature of the amplification reaction mixture is decreased allowing the target sequences and reference sequences to hybridize (FIG. 1B). This annealing step results in the formation of hybridization duplexes of target-target, reference-reference and target-reference sequences. Determining an annealing temperature is well known to the skilled artisan. The PCR primers used in the method are designed to have a $T_m$ that prevents them from binding to the target and reference sequences at this intermediate temperature, so that they don't interfere with cross-hybridization of the mutant (target) and wild-type (reference) sequences. Because of mutations in the target sequence most target sequences end-up in a mismatched structure with the reference sequence, and thus have a lower melting temperature, when heteroduplexed with the reference sequence, than the fully-matched reference/reference homoduplexes.

The target-reference hybridization duplexes are then preferentially denatured by increasing the temperature of the reaction mixture to the Tc (FIG. 1C). The Tc or critical temperature is below the $T_m$ of the reference sequence and can be determined by the methods described herein. In one embodiment, the Tc is about 0.3° C.-5° C. below the $T_m$ of the reference sequence and more preferably about 0.5° C. to 1.5° C. below the $T_m$ of the reference sequence. Generally, the Tc will be about 70-90° C. The target-target hybridization duplexes may also be preferentially denatured if the target sequence has a nucleotide sequence which results in a lower $T_m$ compared to the reference sequence. The Tc is generally applied from about 1 second to 5 minutes, more preferably 2 seconds to 1 minute and most preferably 5 seconds to 30 seconds.

After the preferential denaturing of the target-reference and/or target-target sequence hybridization duplexes, the temperature of the reaction mixture is reduced so as to allow one or more primers to anneal to the target sequence (FIG. 1D). The annealed primers are then extended by a nucleic acid polymerase, thus enriching the target sequence in the population of nucleic acids contained in the sample.

The steps of the method are generally repeated for multiple cycles in order to get sufficient amplification of the target and reference sequences. In one embodiment, the steps of the method are repeated for 5-40 cycles and more preferably 10-30 cycles. The optimal number of cycles can be determined by one of ordinary skill in the art. Preferably, the present methods are performed in a PCR device, more preferably under real-time reaction conditions in a real-time detection PCR device, such as the SMARTCYCLER real-time PCR device (Cepheid, Sunnyvale, Calif.) and the Mx3005P real-time PCR device (Stratagene, La Jolla, Calif.). In this embodiment, the reaction mixture may include a nucleic acid detection agent (e.g., nucleic acid detection dye such as SYBR Green dye or LC-Green dye or a probe operatively coupled to a fluorescent dye) for quantifying and/or monitoring the amplification products of the reaction. Once the enrichment of the target sequence is complete the sample may be further processed, e.g., subjected to a sequencing reaction. The enriched alleles may be further processed by a variety of procedures including: MALDI-TOF, HR-Melting, Di-deoxy-sequencing, Single-molecule sequencing, pyrosequencing, RFLP, digital PCR and quantitative-PCR.

By performing the enrichment method in every PCR-cycle, the amount of mutant sequences (target sequence) is gradually enriched over the sequences (reference sequence). Both homozygous and heterozygous mutations are enriched via the method. Enrichment of mutation-containing sequences by 10-60-fold relative to performing regular PCR at a denaturation temperature of 94° C. is routine. At a given critical denaturation temperature (Tc), the mutation enrichment occurs simultaneously at all sequence positions, albeit with a different efficiency depending on the sequence context and overall size of the PCR amplicon. Both the critical denaturation temperature Tc and the anticipated enrichment at any position are predictable using appropriate DNA melting software and can be verified experimentally. Thus depending on where the mutation is, a somewhat different enrichment can be anticipated, however in all cases a substantial enrichment is achieved and therefore the detection limits of downstream assays improve, e.g., sequencing reactions.

FIG. 2 illustrates an embodiment of the method for enriching a target sequence by subjecting an amplification reaction mixture to multiple alternating steps of annealing and critical denaturing temperature. This embodiment takes advantage of both preferential denaturation at the critical temperate and preferential cross-hybridization at the hybridization temperature.

The amplification reaction mixture, having a target and reference sequence, is first subjected to a first denaturing temperature which is above the $T_i$, of the reference sequence (FIG. 2A).

Next, the sample is cycled between two different temperature incubation steps. In the first incubation step, the temperature is decreased so as to allow the preferential hybridization of the target sequence with the reference sequence (FIG. 2B). In the second incubation step, the temperature is increased to the Tc (FIG. 2C). These first and second steps are then repeated one or more times, more preferably 3-20 times and most preferably 5-10 times.

The preferential hybridization temperature for a given sequence is a temperature at which the wild-type alleles hybridize back to themselves at a faster rate than do the mutation-containing alleles. Because mutated alleles are at a much lower prevalence than wild-type alleles, cross-hybridization of the wild-type alleles with themselves proceeds faster than cross-hybridization of mutant alleles with mutant alleles, or of mutant alleles with alleles (the latter forming a mismatch). As a result, when the PCR temperature is reduced to a cross-hybridization temperature the mutant alleles do not cross-hybridize to the same extent as the wild-type alleles do. In a preferred embodiment, this hybridization temperature or intermediate temperature (the temperature being below the first denaturing temperature and Tc but above the primer annealing/extension temperature, e.g., about 60° C. to 80° C.) is above the $T_m$ of the primer pair, and thus allows the target and reference sequences to hybridize while preventing binding of the primer pair to the target and/or reference sequences.

Next, the temperature of the reaction is increased to the Tc resulting in the target-reference and target-target hybridization duplexes to preferentially denatured (FIG. 2C). The Tc or critical temperature is below the $T_m$ of the reference sequence and can be determined by the methods described herein. In one embodiment, the Tc is about 0.3° C.-5° C. below the $T_m$ of the reference sequence and more preferably about 0.5° C. to 1.5° C. below the $T_m$ of the reference sequence. Generally, the Tc will be about 70-90° C. The target-target hybridization duplexes may also be preferentially denatured if the target sequence has a nucleotide sequence which results in a lower $T_m$ compared to the reference sequence. The Tc is generally applied from about 1 second to 5 minutes, more preferably 2 seconds to 1 minute and most preferably 5 seconds to 30 seconds. This process is repeated for several times, oscillating between the annealing temperature (FIG. 2B) and the critical temperature (FIG. 2C), each time selectively generating more mutant sequences in the single-stranded form than sequences in the single stranded form.

Once the cyclic incubation step is complete, the temperature of the reaction mixture is decreased so as to allow the one or more primers to anneal to the target sequence (FIG. 2D). These primers are then extended by a polymerase, thus enriching the target sequence. The steps of the method are generally repeated for multiple cycles in order to get sufficient amplification of the target and reference sequences. In one embodiment, the steps of the method are repeated for 5-40 cycles and more preferably 10-30 cycles. The optimal number of cycles can be determined by one of ordinary skill in the art. Preferably, the present methods are performed in a PCR device, more preferably under real-time reaction conditions in a real-time detection PCR device.

Once the enrichment of the target sequence is complete the sample may be subjected to further processing. Further processing includes MALDI-TOF, HR-Melting, Di-deoxy-sequencing, Single-molecule sequencing, pyrosequencing, RFLP, digital PCR and quantitative-PCR.

Digital PCR may be used in the detection of ultra-low level mutations in combination with an enrichment procedure. In digital PCR, the DNA sample is diluted down to single molecules, so that in each PCR reaction the starting material is either wild-type or mutant. Following a large number of PCR reactions from the same starting material, mutant molecules are isolated and detected. Fluidigm (South San Francisco, Calif.) sells a variety of digital PCR based systems that can be used with the present invention. Accordingly, real-time enrichment can be performed from single molecules in thousands of parallel enrichment reactions simultaneously, allowing for the identification of the PCR reaction which originated the mutant DNA. Such a system is particularly useful for the detection of ultra-low mutations in cancer genomes. Combination of digital PCR with the enrichment procedure can similarly benefit single molecule sequencing applications.

Nucleic Acid Amplification Reaction

In one embodiment, a nucleic acid sample utilized in the method of the invention comprises genomic DNA having a target and reference sequence. In another embodiment, the nucleic acid sample of the method of the invention comprises a target and reference sequence that were previously amplified in a nucleic acid amplification reaction. The skilled artisan will appreciate that there are many methods available to amplify a nucleic acid. Perhaps the most popular method is the polymerase chain reaction (PCR; for example, see, U.S. Pat. Nos. 4,683,195 and 4,683,202, as well as Saiki et al., Science 230:1350-1354 (1985) and Gyllensten et al., PNAS (USA) 85:7652-7656 (1985)). A preferred variation of the PCR method is asymmetrical PCR (for example, see Mao et al., Biotechniques 27(4):674-678 (1999); Lehbein et al., Electrophoresis 19(8-9):1381-1384 (1998); Lazaro et al., Molec. Cell. Probes 6(5):357-359 (1992); and U.S. Pat. No. 6,197, 499). Other amplification methods include, but are not limited to, strand displacement amplification (SDA) (see, Walker et al., Nuc. Acids Res. 20(7):1691-1696 (1992), as well as U.S. Pat. Nos. 5,744,311, 5,648,211 and 5,631,147), rolling circle amplification (RCA) (see PCT publication WO 97/19193), nucleic acid sequence-based amplification (NASBA) (see Compton, Nature 350:91-92 (1991); as well as U.S. Pat. Nos. 5,409,818 and 5,554,527), transcript mediated amplification (TMA) (see Kwoh et al., PNAS (USA) 86:1173-1177 (1989), as well as U.S. Pat. No. 5,399,491), self sustained sequence replication (3SR) (see Guatelli et al., PNAS (USA) 87:1874-1879 (1990) and ligase chain reaction (LCA) (see U.S. Pat. Nos. 5,427,930 and 5,792,607).

The present method utilizes a modified PCR. PCR, is performed as described in Mullis and Faloona, 1987, Methods Enzymol., 155: 335, herein incorporated by reference. The polymerase chain reaction (PCR) technique, is disclosed in U.S. Pat. Nos. 4,683,202, 4,683,195 and 4,800,159. In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of $10^9$. The PCR method is also described in Saiki et al., 1985, Science 230:1350.

PCR is performed using template DNA (target and reference sequences) (at least 1 fg; more usefully, 1-1000 ng) and at least 25 pmol of oligonucleotide primers. A typical reaction mixture includes: 2 µl of DNA, 25 pmol of oligonucleotide primer, 2.5 µl of a suitable buffer, 0.4 µl of 1.25 µM dNTP, 2.5 units of Taq DNA polymerase (Stratagene) and deionized water to a total volume of 25 µl. PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1 minute). The final extension step is generally carried out for 4 minutes at 72° C., and may be followed by an indefinite (0-24 hour) step at 4° C.

PCR utilizes a nucleic acid polymerase, or enzyme that catalyzes the polymerization of nucleoside triphosphates. Generally, the enzyme will initiate synthesis at the 3'-end of the primer annealed to the target sequence, and will proceed in the 5'-direction along the template. Known DNA polymerases include, for example, E. coli DNA polymerase I, T7 DNA polymerase, Thermus thermophilus (Tth) DNA polymerase, Bacillus stearothermophilus DNA polymerase, Thermococcus litoralis DNA polymerase, Thermus aquaticus (Taq) DNA polymerase and Pyrococcus furiosus (Pfu) DNA polymerase. The term "nucleic acid polymerase" also encompasses RNA polymerases. If the nucleic acid template is RNA, then "nucleic acid polymerase" refers to an RNA-dependent polymerization activity, such as a reverse transcriptase.

In the methods of the invention, the PCR protocol further includes a critical denaturing step. These protocols are fully described herein and are illustrated in FIGS. 1 and 2. Preferably, the enrichment procedures are performed in a PCR device, more preferably under real-time reaction conditions in a real-time PCR device. Real-time reaction conditions further utilize a nucleic acid detection agent (e.g., dye or probe) in order to measure/detect the PCR product as it is produced.

In one embodiment, the enrichment methods are practiced in a multiplex format. Multiplex PCR is when more than one pair of primers is used in a PCR reaction to detect more than one target sequence. The goal of multiplex PCR is to amplify more than one target sequence simultaneously and thereby to save time and minimize expense. It enables the amplification of multiple target sequences in one run. Generally, use of multiplex PCR in conjunction with the present invention for the purpose of enriching the minor alleles in all amplified sequences simultanesously, the primers are designed so that the resulting PCR-amplicons all share about the same Tc (critical denaturation temperature).

Determining the $T_m$ and Tc

The $T_m$ may be defined as the temperature at which one-half of the Watson-Crick base pairs in a duplex nucleic acid molecule are broken or dissociated (i.e., are "melted") while the other half of the Watson-Crick base pairs remain intact in a double stranded conformation. While the "critical temperature", "critical denaturing temperature" or "Tc" refers to a temperature below the $T_m$ of the reference sequence. The Tc is applied to selectively denature the double-stranded target sequence or target sequence/reference sequence double-stranded duplex in a nucleic acid sample so as to allow the selective enrichment of the target sequence during an amplification reaction.

The $T_m$ of a given pair of nucleic acid strands, is indicative of the stability of the strand to strand binding and depends on the strands' complementarity, sequence length, GC content, the presence or absence of mismatches within the double stranded region and other factors of minor importance, e.g. the salt concentration of the sample (Lewin, *Genes V*, Chapter 5, Oxford University Press and Cell Press: New York, (1994) pp. 109-126; SantaLucia, 1998).

The melting point temperature is usually determined experimentally by subjecting the sample to a constitutive increase in temperature and continuously measuring the dissociation of the hybridization duplex into single strands. The dissociation can be detected by a variety of different methods, for example by a shift in UV absorbance, fluorescence of double-stranded DNA binding dyes, by surface plasmon resonance or preferably by means of fluorescence. In the latter case, the hybridization probe is usually labeled with a fluorescent entity, and the generation of a fluorescent signal somehow depends on the formation of the hybridization duplex.

The $T_m$ can be determined experimentally or estimated based on well defined methods known to those of ordinary skill in the art. Methods to observe and analyze nucleic acid denaturation transitions include: measuring the enthalpy change within a sample as it denatures by differential scanning calorimetry (DSC) (Kulinski et al., *Nucleic Acids Res.* 19(9):2449-2455 (1991); Paner et al., *Biopolymers* 29:1715-1734 (1990); Volker et al., *Biopolymers* 50:303-318 (1999)), measuring the fluorescence of covalently attached pairs of fluorophores (Vamosi and Clegg, Biochemistry 37:14300-14316 (1998)), and monitoring the change in hyperchromicity of nucleic acids (Haugland, "In Vitro Applications for Nucleic Acid Stains and Probes", in *Handbook of Fluorescent Probes and Research Chemicals, 6th* ed., Molecular Probes Inc, Eugene Oreg. (1996) pp. 161-174).

$T_m$ values of double stranded nucleic acids can also be observed by monitoring the fluorescence of double-stranded DNA-specific dyes combined with the nucleic acids (Wittwer et al., 1996). Double stranded-specific dyes are nucleic acid-binding fluorophors. Typically, the fluorescence of these dyes increases when bound to duplexed nucleic acids (Wittwer et al., *BioTechniques* 22:176-181 (1997)). Ririe et al. (1997) demonstrated that post PCR products can be differentiated by melting curve analysis using the double stranded nucleic acid binding dye SYBR® Green I. SYBR® Green I binds preferentially to double stranded nucleic acid (Haugland, 1996). Other suitable dyes for determining the $T_m$ of a double stranded nucleic acid include SYBR® Gold, ethidium bromide, acridine orange, propidium bromide, PicoGreen®, Hoechst 33258, Hoechst 33342, Hoechst 34580, YO-PRO®-1 and YOYO®-1. Each of these dyes is commercially available. For example, Chapter 8 of the Molecular Probes (Eugene, Oreg.) catalog *Handbook of Fluorescent Probes and Research Products*, Eighth Edition (on CD-ROM, May, 2001; incorporated herein by reference) lists a host of dyes that may be used in the present invention.

As the skilled artisan will appreciate, the melting of any double stranded nucleic acid structure generally occurs in a substantial proportion of a population of similar nucleic acids over a limited temperature range and will typically have a peak of melting (most rapid transition) at approximately the $T_m$ for that nucleic acid. Therefore, such peaks of change in fluorescence emission can be used to calculate the $T_m$ for double stranded nucleic acids.

A melting temperature profile may be graphically represented by plotting-dF/dT against T, where dF is the change in measured fluorescence emission, dT is the change in temperature of the nucleic acid, and T is the temperature of the nucleic acid. Such a graphic representation will show peaks at temperatures at which the most rapid changes in fluorescence occur, indicating melting temperatures.

Other methods for determining the $T_m$ of a double stranded nucleic acid are known in the art including those described in U.S. Pat. Nos. 7,226,736; and 6,030,115, each of which is hereby incorporated by reference in its entirety.

The $T_m$ can be predicted from empirical equations. $T_m$ is known to depend on the length of the sequence of a nucleic acid forming complementary base pairs (n), the G and C content in the sequence, the concentrations of salt ($\mu$) and the denaturing agent (% FA) in the sample solution, and, in general, follows an empirical equation $T_m=81.5+16.6 \log (\mu)+0.41 (\% GC)-500/n-0.61 (\% FA)$. The $T_m$ can be estimated by a number of methods, for example by a nearest-neighbor calculation as per Wetmur 1991 (Wetmur, J. G. 1991. DNA probes: applications of the principles of nucleic acid hybridization. *Crit Rev Biochem Mol Biol* 26: 227-259, hereby incorporated by reference) and by commercial programs including Oligo™ Primer Design and programs available on the internet.

The "critical temperature" or "Tc" refers to a temperature below the $T_m$ of the reference sequence. The Tc is applied to preferentially denature the double-stranded target sequence duplex or target sequence/reference sequence double-stranded duplex over the reference/reference sequence duplex, so as to allow the selective enrichment of the target sequence during an amplification reaction. The critical temperature takes advantage of the lower $T_m$ of the double stranded target sequence or the target-reference cross hybridized double stranded DNA duplex. When the target sequence and reference sequence cross hybridize, minor sequence differences of one or more single nucleotide mismatch anywhere along a short (e.g., <200 bp) double stranded DNA sequence will generate a small but predictable change in the melting temperature ($T_m$) for that sequence (Lipsky, R. H., et al. (2001) *Clin Chem,* 47, 635-644; Liew, M., et al. (2004) *Clin Chem,* 50, 1156-1164). Depending on the exact sequence context and position of the mismatch, melting temperature changes of 0.5-1.5° C., are common for sequences up to 200 bp. Thus, annealing of the target-reference sequence, because of the mismatches, will essentially have a lower $T_m$ than the known allele (e.g., reference sequence). At least in part, the present invention exploits the small $T_m$ difference between fully-matched and mismatched sequences. Because critical denaturation is performed at every PCR cycle the differential enrichment of mutation-containing alleles is compounded exponentially, and results to a large difference in overall amplification efficiency between mutant and wild-type alleles, at the end of the cycling. The Tc is about 0.1-20° C. below the $T_m$ of the reference sequence. More preferably the Tc is about 0.1-15° C., 0.1-10° C., 0.1-9° C., 0.1-8° C., 0.1-7° C. 0.1-6° C., 0.2 C-5° C., 0.3 C-4.5° C., 0.4-4° C., 0.5-3.5° C., 0.5-3° C., 0.5-3° C., 0.5-2.5° C., 0.5-2° C., 0.5-1.5° C., 0.5-1° C. below the $T_m$ of the reference sequence.

In some embodiments, the Tc can be below the Tm of both the reference sequence and target sequence. For example, in one instance the Tm of a wild-type sequence was 84° C. and the Tm of the mutated sequence was 83.8° C. When a fast version of an enrichment procedure was used the optimal Tc was 83.5° C.

In some preferred embodiments, the Tc is chosen such that it is below the tm of both the reference sequence and all possible target sequences. For example, in one instance the Tm of a wild-type sequence was 84° C. and the tm of sequences mutated at different positions (single point mutations) was 83.8° C., 83.7° C., 83.9° C., 83.6° C., 83.75° C. When a fast version of an enrichment procedure was used the optimal Tc was 83.5° C.

The critical denaturing temperature (Tc) is the temperature below which PCR efficiency drops abruptly for a given nucleic acid sequence. For example, a 167 by p53 sequence amplifies well if the PCR denaturing temperature is set at 87° C., amplifies modestly at 86.5° C. and yields no detectable product if PCR denaturation is set at 86° C. or less.

Like the $T_m$, the Tc for a given sequence can be identified either experimentally, or by calculation. To identify Tc experimentally for a given PCR product, a real-time melting curve in the presence of an intercalating dye (LC-GREEN or SYBR-Green) is performed to obtain the average melting temperature $T_m$ of the sequence (See above with respect to determining $T_m$). Temperatures of about 0.5-1.5° C. less than $T_m$ are usually appropriate critical denaturation temperatures Tc that result to enrichment of target sequences.

One can also estimate the Tc by determining the $\Delta T_m$ for a DNA sequence due to a base-pair mismatch, as would be present in the cross-hybridized target-reference duplex. This difference is from about 0.1° C. to about 12.5° C. as compared to a perfect reference/reference sequence match. Thus, in one embodiment, Tc can be represented by the equation $Tc=T_m-\Delta T_m$ wherein $T_m$ is the melting temperature of the reference/reference sequence duplex and $\Delta T_m$ is the change in the $T_m$ of the reference sequence as the result of one or more base-pair mismatches that may be formed during the cross-hybridization of the target/reference sequences. The $\Delta T_m$ has been found to be dependent on the length of the target/reference sequence duplex, upon the percent guanine-cytosine (% GC) content, and also upon the location of the point mutation or base-pair mismatch in the duplex. For instance, if the mismatch lies toward either end of the duplex, $\Delta T_m$ will generally be lower, typically in the range of about 0.1° C. to about 8° C. If the mismatch resides toward the center of the duplex, $\Delta T_m$ will be relatively higher, typically in the range of about 0.2° C. to about 11° C. The $\Delta T_m$ is generally equivalent to about 0.5° C. to about 1.5° C. per percent base mismatch in the target-reference cross-hybridized duplex. It is to be appreciated that $\Delta T_m$ will vary depending on not only the length of the duplex and location of mutation, but also will vary depending on the specific order of the sequence. Consequently, all such variances are within the scope of the disclosure.

Nucleic Acids of the Invention

Nucleic Acid Sequences Useful in the Invention

The invention provides for methods of enriching a target sequence in a nucleic acid sample and also utilizes primers for amplifying a template nucleic acid sequence.

As used herein, the terms "nucleic acid", "polynucleotide" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases (including abasic sites). There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single-stranded RNA.

The oligonucleotide is not necessarily physically derived from any existing or natural sequence but may be generated in any manner, including chemical synthesis, DNA replication, reverse transcription or a combination thereof. The terms "oligonucleotide" or "nucleic acid" intend a polynucleotide of genomic DNA or RNA, cDNA, semisynthetic, or synthetic origin which, by virtue of its synthetic origin or manipulation: (1) is not associated with all or a portion of the polynucleotide with which it is associated in nature; and/or (2) is linked to a polynucleotide other than that to which it is linked in nature.

In one embodiment, the nucleic acids used in the method contain modified nucleotides so as to increase the denaturing temperature differences between the reference/reference sequence homoduplex and the target/reference sequence heteroduplex. Such modifications would enhance the enrichment of the target sequence. The modified or non-natural nucleotides can be incorporated before or during the enrichment procedure. Modified nucleotides contemplated for use in the methods of the invention include: diamino-purine analogues (e.g. 2'-O-methyl-2,6-diaminopurine), uracil, peptide nucleic acid analogues, biotin-modified analogues of the above, fluorophore-modified analogues of the above, inosine, 7-deazaguanine, 2'-deoxy-2'-fluoro-β-D-arabinonucleic acid (2'F-ANA) nucleotides, locked-nucleic acids (LNAs), ENAs: 2'-O,4'-C-ethylene-bridged nucleic acids and others. The modified nucleotides can be incorporated into any of the nucleic acids of the invention including, template, primer and probe nucleic acids.

These modifications may increase the $T_m$ difference between matched and mismatched bases and thereby increasing the enrichment obtained with the present methods. For example, locked nucleic acids represent a class of conformationally restricted nucleotide analogues described, for example, in WO 99/14226, which is incorporated by reference, increase the melting temperature of a nucleic acid. Oligonucleotides containing the locked nucleotide are described in Koshkin, A. A., et al., *Tetrahedron* (1998), 54: 3607-3630) and Obika, S. et al., *Tetrahedron Lett.* (1998), 39: 5401-5404), both of which are incorporated by reference. Introduction of a locked nucleotide into an oligonucleotide improves the affinity for complementary sequences and increases the melting temperature by several degrees (Braasch, D. A. and D. R. Corey, *Chem. Biol.* (2001), 8:1-7). The invention can be carried out with any of the LNAs known in the art, for example, those disclosed in WO 99/14226 and in Latorra D, et al., 2003. Hum. Mutat. 22: 79-85, both of which are incorporated herein by reference.

Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength, and incidence of mismatched base pairs. Stability of a nucleic acid duplex is measured by the melting temperature, or "$T_m$".

The invention provides for oligonucleotide primers for amplifying a template nucleic acid sequence.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

Oligonucleotide primers useful according to the invention are single-stranded DNA or RNA molecules that are hybridizable to a template nucleic acid sequence and prime enzymatic synthesis of a nucleic acid strand. The primer is complementary to a portion of a target molecule present in a pool of nucleic acid molecules. It is contemplated that oligonucleotide primers according to the invention are prepared by synthetic methods, either chemical or enzymatic. Alternatively, such a molecule or a fragment thereof is naturally-occurring, and is isolated from its natural source or purchased from a commercial supplier. Oligonucleotide primers are 5 to 100 nucleotides in length, ideally from 17 to 40 nucleotides, although primers of different length are of use. Primers for amplification are preferably about 17-25 nucleotides. Primers useful according to the invention are also designed to have a particular melting temperature ($T_m$) by the method of melting temperature estimation. Commercial programs, including Oligo™, Primer Design and programs available on the internet, including Primer3 and Oligo Calculator can be used to calculate a $T_m$ of a nucleic acid sequence useful according to the invention. Preferably, the $T_m$ of an amplification primer useful according to the invention, as calculated for example by Oligo Calculator, is preferably between about 45 and 65° C. and more preferably between about 50 and 60° C.

Typically, selective hybridization occurs when two nucleic acid sequences are substantially complementary (at least about 65% complementary over a stretch of at least 14 to 25 nucleotides, preferably at least about 75%, more preferably at least about 90% complementary). See Kanehisa, M., 1984, Nucleic Acids Res. 12: 203, incorporated herein by reference. As a result, it is expected that a certain degree of mismatch at the priming site is tolerated. Such mismatch may be small, such as a mono-, di- or tri-nucleotide. Alternatively, a region of mismatch may encompass loops, which are defined as regions in which there exists a mismatch in an uninterrupted series of four or more nucleotides.

In one embodiment, the enrichment procedures can be used in combination with peptide nucleic acid (PNA) primers so as to increase the sensitivity of mutation enrichment. The PNAs are used to suppress amplification of the wild-type (reference) sequences only. In this embodiment, primers may be synthesized so as to distinguish between a target (mutant) sequence and a reference sequence. The PNA based primers recognize and bind the complementary wild-type sequence with a higher thermal stability and specificity than primers which bind the mutated sequence. This not only increases the Tm difference between the PNA primer-reference nucleic acid and regular primer-target nucleic acid but also prevents the PNA based primer from being extended by a DNA polymerase, thus resulting in a further enrichment of the target sequence. Such assays are known and the art and described in Orum et al. *Nucleic Acids Research,* 21(23): 5332-5336 (1993).

Oligonucleotide primers can be designed with these considerations in mind and synthesized according to the following methods.

Oligonucleotide Primer Design Strategy

The design of a particular oligonucleotide primer for the purpose of sequencing or PCR, involves selecting a sequence that is capable of recognizing the target sequence, but has a minimal predicted secondary structure. The oligonucleotide sequence may or may not bind only to a single site in the target nucleic acid. Furthermore, the $T_m$ of the oligonucleotide is optimized by analysis of the length and GC content of the oligonucleotide. Furthermore, when designing a PCR primer useful for the amplification of genomic DNA, the selected primer sequence does not demonstrate significant matches to sequences in the GenBank database (or other available databases).

The design of a primer useful according to the invention, is facilitated by the use of readily available computer programs, developed to assist in the evaluation of the several parameters described above and the optimization of primer sequences. Examples of such programs are "PrimerSelect" of the DNAStar™ software package (DNAStar, Inc.; Madison, Wis.), OLIGO 4.0 (National Biosciences, Inc.), PRIMER, Oligonucleotide Selection Program, PGEN and Amplify (described in Ausubel et al., 1995, Short Protocols in Molecular Biology, 3rd Edition, John Wiley & Sons).

In a preferred embodiment, the primers of the invention are designed so as to have a $T_m$ below the temperature applied during the target/reference sequence cross-hybridization step. Thus, in this embodiment the primers do not anneal to the target or reference sequences during this hybridization step (See FIG. 1). In one embodiment, the $T_m$ of the primers is 5-10° C. below the cross-hybridization annealing step temperature.

Synthesis

The primers themselves are synthesized using techniques that are also well known in the art. Methods for preparing oligonucleotides of specific sequence are known in the art, and include, for example, cloning and restriction digest analysis of appropriate sequences and direct chemical synthesis. Once designed, oligonucleotides are prepared by a suitable chemical synthesis method, including, for example, the phosphotriester method described by Narang et al., 1979, Methods in Enzymology, 68:90, the phosphodiester method disclosed by Brown et al., 1979, Methods in Enzymology, 68:109, the diethylphosphoramidate method disclosed in Beaucage et al., 1981, Tetrahedron Letters, 22:1859, and the solid support method disclosed in U.S. Pat. No. 4,458,066, or by other chemical methods using either a commercial automated oligonucleotide synthesizer (which is commercially available) or VLSIPS™ technology. The primers may also be synthesized with modified nucleic acids by methods well known in the art.

Samples

As used herein, "sample" refers to any substance containing or presumed to contain a nucleic acid of interest (target and reference sequences) or which is itself a nucleic acid containing or presumed to contain a target nucleic acid of interest. The term "sample" thus includes a sample of nucleic acid (genomic DNA, cDNA, RNA), cell, organism, tissue, fluid, or substance including but not limited to, for example, plasma, serum, spinal fluid, lymph fluid, synovial fluid, urine, tears, stool, external secretions of the skin, respiratory, intestinal and genitourinary tracts, saliva, blood cells, tumors, organs, tissue, samples of in vitro cell culture constituents, natural isolates (such as drinking water, seawater, solid materials), microbial specimens, and objects or specimens that have been "marked" with nucleic acid tracer molecules.

Nucleic acid sequences of the invention can be amplified from genomic DNA. Genomic DNA can be isolated from tissues or cells according to the following method. Alternatively nucleic acids sequences of the invention can be isolated from blood by methods well known in the art.

To facilitate detection of a variant form of a gene from a particular tissue, the tissue is isolated. To isolate genomic DNA from mammalian tissue, the tissue is minced and frozen in liquid nitrogen. Frozen tissue is ground into a fine powder with a prechilled mortar and pestle, and suspended in digestion buffer (100 mM NaCl, 10 mM Tris-HCl, pH 8.0, 25 mM EDTA, pH 8.0, 0.5% (w/v) SDS, 0.1 mg/ml proteinase K) at 1.2 ml digestion buffer per 100 mg of tissue. To isolate genomic DNA from mammalian tissue culture cells, cells are pelleted by centrifugation for 5 min at 500×g, resuspended in 1-10 ml ice-cold PBS, repelleted for 5 min at 500×g and resuspended in 1 volume of digestion buffer.

Samples in digestion buffer are incubated (with shaking) for 12-18 hours at 50° C., and then extracted with an equal volume of phenol/chloroform/isoamyl alcohol. If the phases are not resolved following a centrifugation step (10 min at 1700×g), another volume of digestion buffer (without proteinase K) is added and the centrifugation step is repeated. If a thick white material is evident at the interface of the two phases, the organic extraction step is repeated. Following extraction the upper, aqueous layer is transferred to a new tube to which will be added ½ volume of 7.5M ammonium acetate and 2 volumes of 100% ethanol. The nucleic acid is pelleted by centrifugation for 2 min at 1700×g, washed with 70% ethanol, air dried and resuspended in TE buffer (10 mM Tris-HCl, pH 8.0, 1 mM EDTA, pH 8.0) at 1 mg/ml. Residual RNA is removed by incubating the sample for 1 hour at 37° C. in the presence of 0.1% SDS and 1 μg/ml DNase-free RNase, and repeating the extraction and ethanol precipitation steps. The yield of genomic DNA, according to this method is expected to be approximately 2 mg DNA/1 g cells or tissue (Ausubel et al., supra). Genomic DNA isolated according to this method can be used according to the invention.

The target DNA may also be extracted from whole blood. For example, blood may be drawn by standard methods into a collection tube, preferably comprising siliconized glass, either without anticoagulant for preparation of serum, or with EDTA, sodium citrate, heparin, or similar anticoagulants, most preferably EDTA, for preparation of plasma. The preferred method, although not absolutely required, is that plasma or serum be fractionated from whole blood. Plasma or serum may be fractionated from whole blood by centrifugation, preferably gentle centrifugation at 300 to 800×g for 5 10 minutes, or fractionated by other standard methods. Since heparin may interfere with PCR, use of heparinized blood may require pretreatment with heparinase. Thus, EDTA is the preferred anticoagulant for blood specimens. Either freshly-collected blood plasma or serum, or frozen (stored) and subsequently thawed plasma or serum can be used in the methods of the invention. Stored plasma or serum should be kept at −20° C. to −70° C., and freshly-collected plasma or serum kept refrigerated or maintained on ice until use. The DNA may then be extracted by methods well known in the art as well as those described herein.

Diagnostic Assays

The invention provides a method for enriching target sequences from a patient sample, for diagnosis, detection, monitoring, evaluation or treatment of a disorder, in particular a neoplastic or proliferative disease in an animal or a human. In a preferred embodiment, the nucleic acid is derived from a nucleic acid encoding an oncogene or other tumor-associated DNA.

The preferential enrichment of the target sequence allows for the further analysis or manipulation of the DNA. For example, the enriched alleles may be analyzed to define the characteristics of the cell from which the DNA originates. Any of several methods may be used, dependent upon the desired information, including nucleic acid sequencing, RFLP, digital PCR, spectroscopy including proton NMR spectroscopy, biochemical analysis, and immunologic analysis. In one embodiment, amplified DNA is isolated by excising mutant DNA bands from an agarose gel, reamplified, cloned into a plasmid vector, for example the pGEM-T vector plasmid (Promega) and sequenced using a commercial kit such as Sequenase 2.0 (USB). Analysis to define the characteristics of the target DNA, and thus for example a tumor, affords a wide array of clinical utility, including the description, characterization, or classification of the cell (e.g., tumor), whether known or occult, such as by tissue of origin, by type (such as premalignant or malignant), phenotype, and genotype, and by description or characterization of tumor behavior, physiology and biochemistry, as to gain understanding of tumor invasiveness, propensity to metastasize, and sensitivity or resistance to various therapies, thereby allowing the prediction of response to either ongoing or planned therapy and, further, allowing evaluation of prognosis. Comparison of the characteristics of target DNA to previous biopsy or surgical specimens permits further evaluation of tumor heterogeneity or similarity in comparison to that specimen, and thus evaluation of tumor recurrence.

Also following the selective enrichment of the target sequence, complimentary ribonucleic acid (RNA) may be transcribed or manufactured from the DNA. In a preferred embodiment, transcription of RNA is performed by employing a primer with an RNA polymerase promoter region joined to the standard primer sequence for the DNA of interest in the amplification reaction (step three). RNA complimentary to the DNA is then transcribed from the attached promoter region. In an alternative method, amplified allele DNA is cloned into an expression vector, and RNA complimentary to the DNA is transcribed. Furthermore, as an optional preferred embodiment, the complimentary RNA is used in an in vitro translation reaction to manufacture tumor-associated or tumor-specific protein.

Characterization of the allele, amplification of tumor-derived or tumor-associated DNA, and characterization, transcription of complimentary RNA, and translation to tumor-associated or tumor-specific protein, provides significant utility, both in the assignment of therapy and in the development of tumor-specific therapies. Sequencing of extracellular DNA or transcription of complementary RNA allows assignment or development of antisense compounds, including synthetic oligonucleotides and other antisense constructs appropriately specific to the extracellular DNA, such as by construction of an expression plasmid such as by adapting the method of Aoki et al. (1995, Cancer Res. 55: 3810 3816). Similarly, defining tumor characteristics allows assignment of specific monoclonal antibody or vaccine therapies appropriately specific to the amplified DNA. Production of corresponding immunologic protein can be used in the development of tumor-specific monoclonal antibodies. Similarly, translated protein can be used in tumor-specific vaccine development.

Of particular value, the invention allows the development and application of these tumor-specific therapies or diagnostics even when only premalignant tumors, early cancers, or occult cancers are present. Thus, the invention allows therapeutic intervention when tumor burden is low, immunologic function is relatively intact, and the patient is not compromised, all increasing the potential for cure.

Further Processing of Enriched Sequences

Combination of the present methods with MALDI-TOF, High-Resolution Melting or Single Molecule Sequencing, would address 3 distinct needs in mutation detection: Rapid detection of somatic mutations known or suspected of correlating with clinical outcome (MALDI-TOF); rapid scanning of individual patient samples for unknown somatic mutations (HR-Melting), followed by selective sequencing of few exons; and massively-parallel sequencing (Single Molecule Sequencing, SMS) of multiple genes in 'difficult samples', i.e. in samples from tumors with heterogeneity, stromal contamination or bodily fluids where clinically relevant mutations can be at the 0.5-5% level.

Mass Spectrometry

In one embodiment, an enriched target sequence is subjected to sequencing by MALDI-TOF. Mass spectrometry (MS) has emerged as a powerful tool in DNA sequencing. Mass spectrometers produce a direct mass measurement, which can be acquired in seconds or minutes in the femtomolar to picomolar range. Matrix-assisted laser desorption/ionization (MALDI) time-of-flight (TOF) MS has been successfully used for fast DNA sequencing and the efficient size determination of DNA molecules. The advent of MALDI-TOF MS has made it easier to ionize intact large DNA molecules and measure their mass-to-charge ratios. Single-stranded and double-stranded polymerase chain reaction (PCR®) products of 500 nucleotide (nt) in length have been detected by MALDI-TOF MS. Using optimized matrix-laser combinations that reduce DNA fragmentation, infrared MALDI mass spectra of synthetic DNA, restriction enzyme fragments of plasmid DNA, and RNA transcripts up to a size of 2180 nt have been reported with an accuracy of ±0.5-1%. Although large oligomers have been detected by MALDI-TOF MS, it is generally accepted that up to a 100-mer is routine at present.

For several genes, clinically-important mutations do not occur randomly in the genome (for example, gain-of-function point mutations occurring in most known oncogene). Instead, changes affecting a relatively small number of codons often account for the majority of somatic mutations. In principle, then, a limited number of judiciously designed genetic assays should effectively interrogate a large proportion of clinically-relevant mutations. For example, Garraway and colleagues (Thomas, R. K., et al. (2007) *Nat Genet,* 39, 347-351) showed that 16-44 MALDI-TOF assays per gene in RAS, EGFR and BRAF captured 90%-99% of the mutation prevalence observed thus far for these genes in human malignancies. Therefore, it is proposed that high-throughput genotyping might provide an effective means to detect critical and/or 'targetable' cancer mutations on a large scale in clinical specimens. MALDI-TOF is ideally suited for detection of previously identified mutations in non-heterogeneous tumor samples. However, while there is no question on the reliability of MALDI-TOF for germline mutation or SNP-identification, experience in detecting somatic mutations is relatively recent. Thus, the reliability of MALDI-TOF decreases substantially when heterogeneous samples with <10% mutated cells are used (e.g. pancreatic, lung or prostate cancer) or when DNA from bodily fluids are to be screened. By improving sensitivity, the present enrichment method enables MALDI-TOF to detect low-level somatic mutations and will also provide the required reliability that is necessary for mainstream surgical tumor sample screening.

High Resolution Melting

In another embodiment, an enriched target sequence is subjected to high resolution melting. Genes that contain clinically-relevant mutations at numerous positions along exons, such as p53, are easier screened via mutation scanning rather than individual mutation genotyping. HR-Melting is a high throughput mutation scanning technology introduced in the last few years, with excellent capabilities for discovering SNPs or germline mutations (Chou, L. S., et al. (2005); *Am J Clin Pathol,* 124, 330-338; Wittwer, C. T., et al. (2003); *Clin Chem,* 49, 853-860; Reed, G. H. and Wittwer, C. T. (2004); *Clin Chem,* 50, 1748-1754).

Immediately following PCR amplification of a genomic region of interest in the presence of an intercalating fluorescent dye (LC Green or Sybr-Green) the presence of a mutation is identified in real-time by careful melting curve analysis and comparison to wild-type without any post-amplification treatments. In addition, high-resolution melting analysis accomplishes simultaneous gene scanning and mutation genotyping (i.e. SNP identification) in a fraction of the time required when using traditional methods, while maintaining a closed-tube environment. The PCR requires <30 min (capillaries) or 1.5 h (96- or 384-well plates) and melting acquisition takes 1-2 min per capillary or 5 min per plate.

However, as with MALDI-TOF, the advantages of using HR-Melting cannot be exploited for somatic mutations below approximately ~20% mutant-to-wild-type ratios, thereby several classes of clinical samples cannot be screened reliably via HR-Melting. By increasing the detection limits, the present invention enables the convenience and throughput of HR-Melting to be applied for mainstream surgical tumor sample screening and also for detecting low-level somatic mutations in 'difficult' clinical samples with stromal contamination or DNA from bodily fluids.

Single Molecule Sequencing

In another embodiment, the enriched target sequence is subjected to single molecule sequencing (Thomas, R. K., et al. (2006); *Nat Med,* 12, 852-855). The capabilities of Single Molecule Sequencing would also benefit from incorporation of the present invention. For example, for mutation-screening in patient samples, PCR of selected exons in a regular PCR machine from genomic DNA is still required prior to initiating second generation sequencing. Further, detection of mutations at the level of 1-5% mutant-to-wild-type ratio in clinical samples requires repeated sequencing of numerous 'individual events' in order to achieve acceptable statistics. This ultimately reduces the throughput capabilities, and for mutations at the level of 1% just 10-20 sequences can be screened simultaneously, as opposed to ~4,000 sequences if the mutations were prevalent (per 454 Life Sciences, Technical Service). By performing the present invention prior to single molecule sequencing the prevalence of mutations will increase by 1-2 orders of magnitude as a fraction of the overall number or alleles, thereby increasing the throughput of single molecule sequencing to an equivalent degree.

In one embodiment, the method of selective enrichment is applied during the in-emulsion stage of a single molecule sequencing reaction. In this embodiment, the enriched target sequences are then subjected to pyrosequencing.

Primer Extension

In another embodiment, the enriched target sequence is subjected to a primer extension sequencing reaction. In primer extension, oligonucleotides are used to assess variation in sequence at a predetermined position thereof relative to a nucleic acid, the sequence of which is known. A sample oligonucleotide is provided as a single stranded molecule, the single stranded molecule is mixed with an inducing agent, a labeled nucleotide, and a primer having a sequence identical to a region flanking the predetermined position to form a mixture, the mixture having an essential absence of nucleotides constituted of bases other than the base of which the labeled nucleotide is constituted. The mixture is then subjected to conditions conducive for the annealing of the primer to the single-stranded molecule and the formation of a primer extension product incorporating the labeled nucleotide, and the mixture is analyzed for the presence of primer extension product containing labeled nucleotide (U.S. Pat. No. 5,846, 710).

Buffers

Inclusion of organic solvents to increase the $T_m$ differences between mismatched and matched duplexes in the amplification method of the current invention is contemplated. The inclusion of certain organic solvents can improve enrichment of the target sequence. For example, inclusion of organic solvents may increase the denaturation temperature difference between reference and target DNA sequences and thus aid the preferential amplification of the target sequence. Organic solvents such as DMSO, formamide, betaine or glycerol (Pomp, D. and Medrano, J. F., *Biotechniques*, 10, 58-59 (1991)) can increase the $T_m$ difference between matched (reference/reference) and mismatched (target/reference) sequences. Accordingly, since the intermediate hybridization step (cross-hybridization) of the present invention forms target-reference sequences containing mismatches, inclusion of organic solvents to the degree that they do not inhibit the action of polymerase is advantageous. Therefore, in some embodiments, the reaction mixture is supplemented with DMSO, formamide, betaine, glycerol, or a combination thereof, at levels of 1-10% volume to volume, or preferably 3-8% volume to volume, or most preferably 5-6% volume to volume. Example 8 illustrates the use of DMSO in an enrichment method.

Another practical advantage of using organic solvents is that the Tc that is appropriate for a given sequence changes upon using an organic solvent in the reaction. Thus, while in the absence of DMSO the Tc for a sequence is 83.5° C., in the presence of 3% DMSO the Tc is 80.5° C. As a result, by adding a different amount of DMSO or other solvent to different sequences, one can ensure that the Tc is the same for all sequences. This is useful for running numerous enrichment reactions for a variety of sequences on a single PCR machine-run, since the denaturation temperature is then the same for all.

EXAMPLES

Example 1

Materials and Methods for Enriching a Target Sequence

Figure 3:
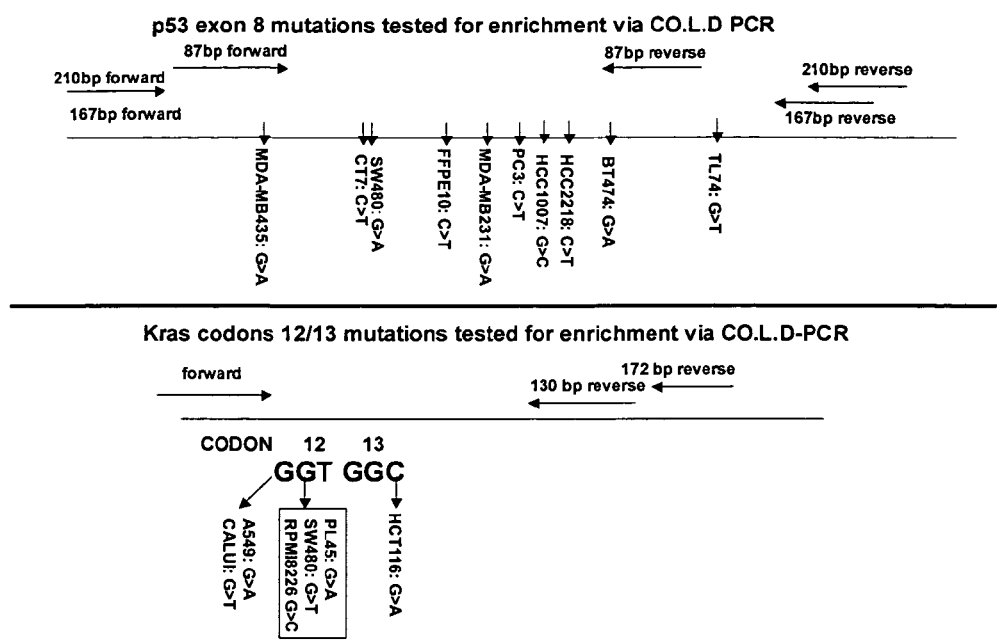
FIG. 3 illustrates the p53 and Kras mutations tested for enrichment via a target sequence enrichment protocol

Sequences used for validation of COLD-PCR: To validate the present invention, a series of genomic DNA and cell lines containing mutations at different positions of p53 exon 8 and Kras exon 2 (codons 12-13) were used (FIG. 3). The p53 exon 8 mutations correlate with poor prognosis in lung cancer and are low-prevalence mutations in the plasma of cancer patients. Similarly, Kras mutations have prognostic significance in lung adenocarcinoma.

Enrichment protocol and primers: PCR was performed in the presence of 0.1× LC-Green intercalating dye and followed in real-time in a Cepheid machine. Real-time-follow-up of PCR is not necessary but is convenient so it was adopted for all experiments.

For the 167 by p53 sequence normal PCR was first performed for 10 cycles in order to generate sufficient product for use in the enrichment protocol. A Cepheid machine was programmed with the following cycling parameters: 95° C., 120 sec; (95° C., 15 sec/55° C. fluorescence readout ON, 30 sec/72° C., 1 min extension)×10 cycles.

The resulting PCR product was then diluted 1:1000 and subjected to the below enrichment protocol which is also illustrated in FIG. 1:

95° C., 15 sec; 70° C. for 120 sec; denaturation at a Tc=86.5° C. for 3 sec; 55° C. fluorescence readout ON for 30 sec; then 72° C., 1 min extension for 30 cycles.

In order to prepare the PCR product for Sanger dideoxy-sequencing the product was treated with exonuclease I and Shrimp Alkaline Phosphatase. The following primers were used in the sequencing method:

```
167 bp fragment:
                                          (SEQ ID NO: 1)
  5'- GCT TCT CTT TTC CTA TCC TG -3' forward;

(SEQ ID NO: 2)
  5'- CTT ACC TCG CTT AGT GCT -3' reverse
```

For the 87 by and 210 by p53 fragments and the 135 bp, Kras fragments the enrichment protocol was as described above but the critical denaturation temperatures were set at Tc=83.5, 87.5, and 80° C., respectively. The primers used in the sequencing reaction were:

```
                                          (SEQ IN NO: 3)
  5'- TGG TAA TCT ACT GGG ACG-3' forward;

(SEQ ID NO: 4)
  5' CGG AGA TTC TCT TCC TCT -3' reverse
  (87 bp p53 exon 8 fragment)

(SEQ ID NO: 1)
  5'- GCT TCT CTT TTC CTA TCC TG -3' forward;

(SEQ ID NO: 5)
  5'- TAA CTG CAC CCT TGG TC -3' reverse
  (210 bp p53 exon 8 fragment)

(SEQ ID NO: 6)
  5'-AACTTGTGGTAGTTGGACCT-3' forward;

(SEQ ID NO: 7)
  5'-CTCTATTGTTGGATCATATT-3' reverse
  (Kras exon 2 fragment).
```

The reproducibility of all enrichment protocols was tested in 3-6 independent experiments.

Figure 4:
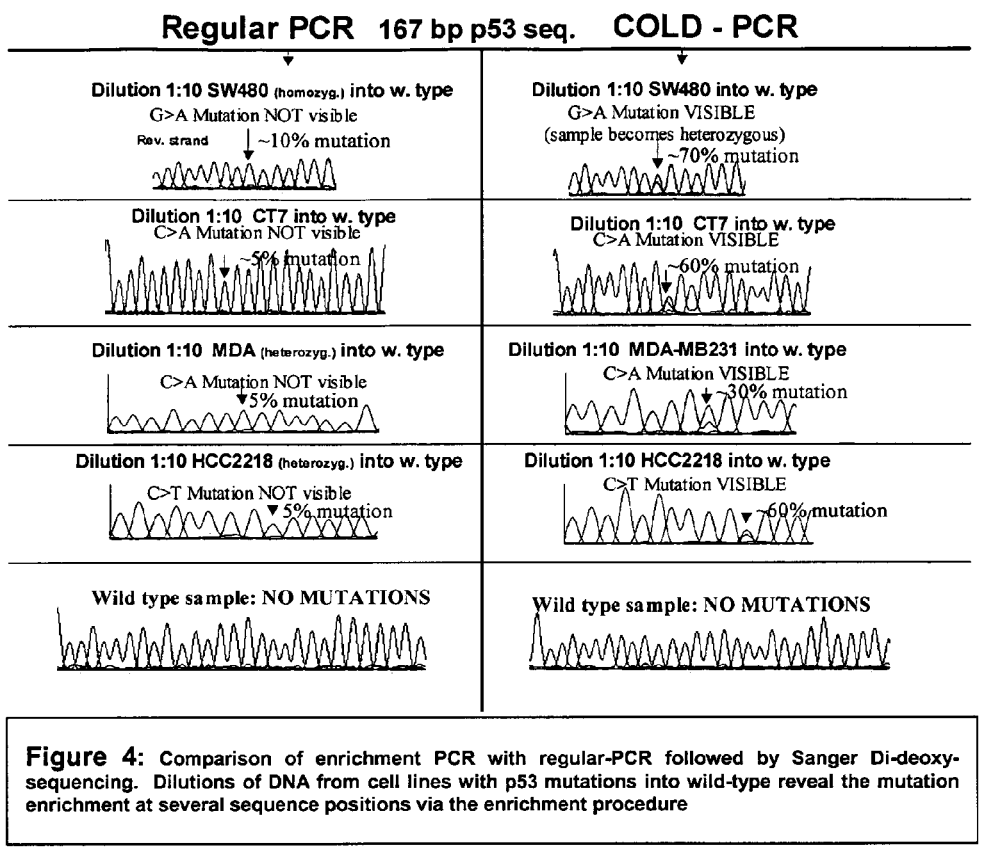
FIG. 4 illustrates the enrichment of p53 mutant alleles with a target sequence enrichment protocol.

Results p53 exon 8 mutations: When the enrichment protocol utilizing a critical denaturation temperature Tc=86.5° C. was applied for the 167 by exon 8 fragment, the enrichment was evident for all mutations tested. FIG. 4 depicts representative results. For example, DNA from HCC cells initially diluted in wild-type cells down to 5% mutant-to-wild-type ratio, becomes ~70% mutant-to-wild-type ratio following the enrichment protocol, as estimated by observing the sequencing chromatogram (i.e. enrichment by a factor of ~14). Similarly, DNA from SW480 cells (homozygous G>A mutation at codon 273) diluted by a factor of 10 into wild-type is enriched by a factor of ~7 following the enrichment procedure. Enrichment by a factor of ~12 for the CT7 sample (heterozygous C>A mutation) and by a factor of 6 for the MDA-MB231 sample (heterozygous C>T mutation) were also observed. The wild-type p53 sample, amplified via the enrichment method indicated no mutation (FIG. 4). Over all the p53 mutations that were studied for the 167 by fragment, as listed on FIG. 2, the enrichment varied by 5-14-fold. Thus, the enrichment procedure increased the prevalence of all the mutation-containing sequences irrespective of where the mutation lies.

Figure 5:
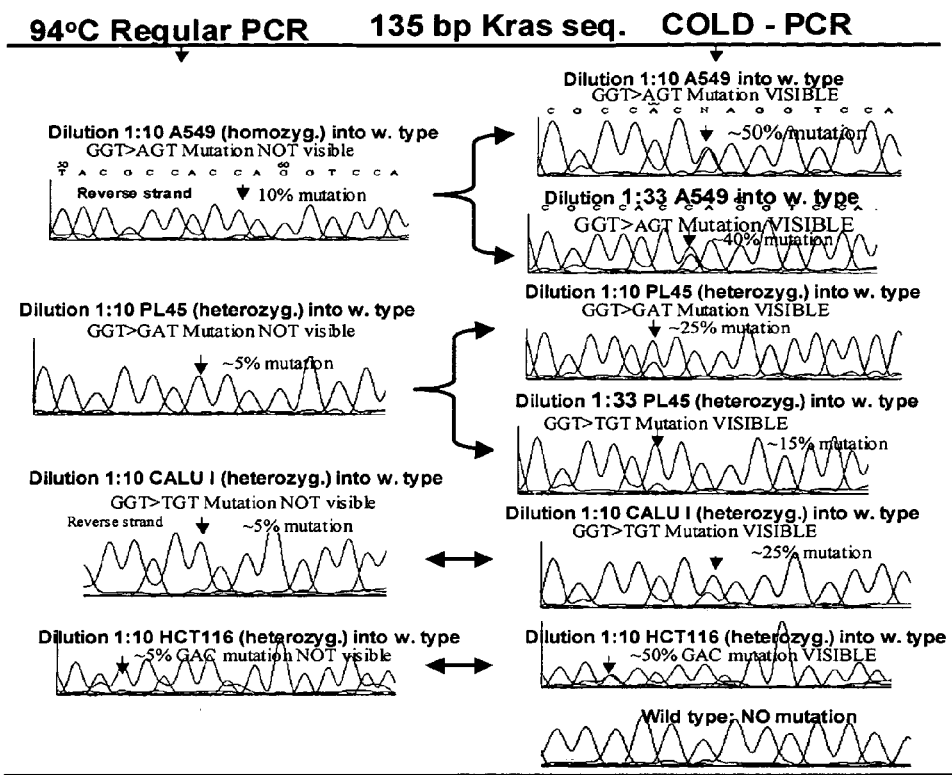
FIG. 5 illustrates the enrichment of Kras mutant alleles with a target sequence enrichment protocol.

Kras codon 12/13 mutations: FIG. 5 illustrates the results of the 135 by fragment from Kras. The results were compared to regular nested PCR performed at a denaturation temperature of 94° C. and followed by Sanger sequencing. FIG. 5 illustrates that mutations down to 33% mutant-to-wild-type can be clearly detected using Sanger sequencing.

Example 2

Sanger Sequencing of Clinical Samples

Figure 6:
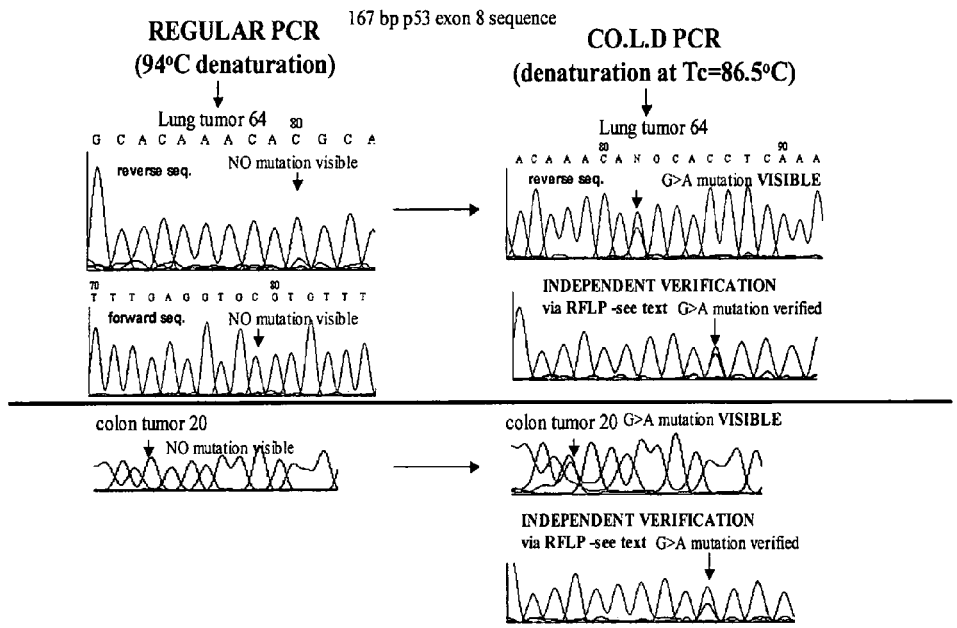
FIG. 6 illustrates the enrichment of mutant alleles in clinical samples from lung and colon tumors.

To apply the present invention for the analysis of clinical samples, 20 colon tumor and lung adenocarcinoma clinical samples that were previously sequenced following regular PCR were subjected to the enrichment protocol and sanger sequencing as described in Example 1. Results indicated that all mutations identified via regular PCR-Sanger sequencing were also identified via the enrichment procedure followed by sequencing. However, the enrichment procedure also identified mutations that were missed by regular sequencing. FIG. 6 depicts 2 clinical samples, TL64 and CT20, where low-prevalence G>A mutations were detected via the enrichment protocol-Sanger sequencing of p53 exon 8, codon 273, but which were not detected by sequencing following regular PCR. An independent verification of the presence of mutations was conducted using RFLP-based sequencing.

Further, a p53 exon 8 (G>A) mutation was detected in plasma-circulating DNA from 5 colon cancer patients via the enrichment procedure-Sanger sequencing, but not via regular PCR-Sanger sequencing. Next, p53 (C>T) mutations that were missed by regular sequencing were also revealed using DNA obtained from a formalin-fixed (FFPE) specimen obtained from a non-small-cell lung cancer patient (NSCLC) (FIG. 6). The bottom chromatograph in FIG. 6 demonstrates the detection of Kras codon 12 mutations in another FFPE sample obtained from a NSCLC patient. The mutations identified via the enrichment procedure were subsequently independently verified from genomic DNA via RFLP methods. Thus, relevant mutations missed by regular PCR-sequencing become readily detectable using COLD-PCR-sequencing.

Example 3

Mutations that Decrease the $T_m$ can be Enriched without the Mismatch Annealing Step The dependence of PCR on the nucleotide sequence is so pronounced when the denaturation temperature is set at the critical temperature (Tc) that even without forming a mismatch during PCR there is enrichment of those mutations that decrease the $T_m$. Thus, when a G and an A allele are present, the A-allele will be enriched during COLD-PCR as this decreases the $T_m$ of the allele. To demonstrate this point, and to also examine the dependence of the enrichment on the size of the examined sequence, an 87 by fragment and a 210 by fragment containing the same mutations as the 167 by fragment from p53 exon 8 were examined (FIG. 3). As with the 167 by fragment, these two fragments were amplified from the initial p53 exon 8 amplicon via nested PCR followed by the enrichment protocol. However, in this case a truncated version of the amplification protocol of Example 1 was used, but the mismatch-forming step at 70° C. as well as the 94° C. step were both omitted (critical denaturation temperatures Tc=83.5° C. for 87 by fragment and Tc=87.5 for 210 by fragment). Therefore, in this version of the enrichment protocol the PCR cycles only between the critical denaturation temperature (Tc), the primer binding step (e.g. 55° C.) and the primer synthesis step (e.g. 72° C.).

Figure 7:
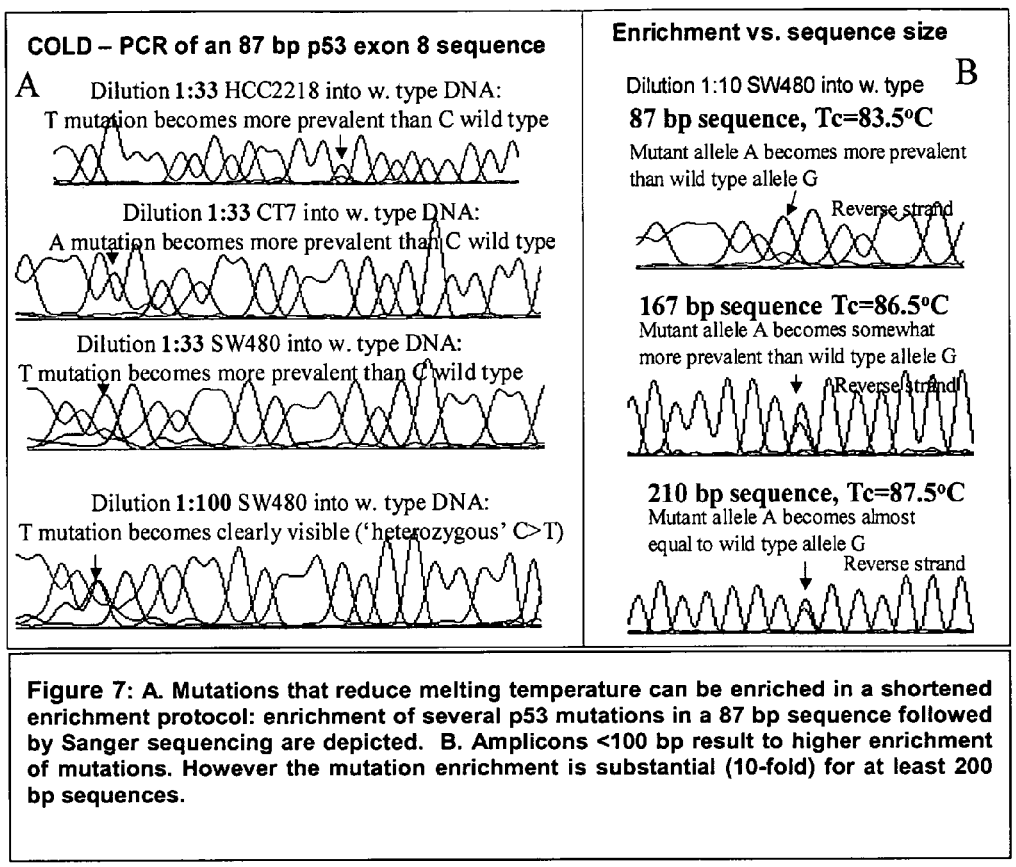
FIG. 7 illustrates the enrichment of mutant alleles by an embodiment of the enrichment protocol which lacks the mismatch-forming step.

FIG. 7A demonstrates sequencing chromatograms for the 87 by fragment (either the forward or the reverse sequencing were performed depending where the mutation lies on the 87 by sequence). The data indicates that, using this version of the modified enrichment protocol, enriches the 87 by fragment 20-50 fold. For example, a 1% initial dilution of mutant-to-wild-type DNA of SW480 DNA resulted in 50% mutant-to-wild-type following the enrichment i.e. ~50-fold enrichment. The subsequent Sanger sequencing revealed a 'heterozygous' sequence. The affect of size on enrichment via the abbreviated the enrichment protocol is depicted in FIG. 7B. This data illustrates that enrichment is highest for fragments <100 bp, but still clearly evident (~8-10 fold) for fragments up to 210 bp.

Example 4

Mutations that Increase or Decrease the $T_M$ can be Enriched Via the Full Enrichment Method Although most (~70%) mutations encountered in diverse cancer samples decrease the $T_m$, ~15% of mutations increase the $T_m$ (e.g. A>G) while ~15% retain the $T_m$ (e.g. G>C). In order to be able to enrich for all possible mutations, including both G>A and A>G mutations and deletions, the full enrichment program is preferred (FIG. 1). To demonstrate the ability to enrich target sequences having mutations that increase or decrease the $T_m$, 167 by p53 exon 8 fragments with either C or T nucleotide (wild-type vs. HCC cell line) were amplified via the enrichment protocol of FIG. 1.

Two mixtures were formed, one with the C allele in minority (C:T 1:10) and another with the T allele in minority (T:C 1:10). Following the enrichment procedure, or alternatively regular PCR, the products were sequenced. In both cases the minor allele was enriched, i.e. either the C or the T depending on which one was more dilute before amplification. Presumably the mismatched sequence has a lower melting temperature than either the C or the T allele, therefore by performing the protocol of FIG. 1 the mismatched sequences are always denatured preferentially. Therefore, by forming a mismatch at an intermediate temperature (~70° C.) during the enrichment protocol there is always enrichment of the minor allele even if the specific nucleotide change tends to increase the local $T_m$.

Example 5

MALDI-TOF Sequencing

The present invention is also expected to improve most other PCR-based technologies, including MALDI-TOF for somatic mutation detection. To demonstrate this point, the same model applied in Example 1, for Sanger sequencing to identify specific p53 exon 8 mutations using serial dilutions of mutation-containing cell lines into wild-type samples, was used to compare the enrichment protocol vs. regular PCR followed by MALDI-TOF.

Following the enrichment protocol or regular PCR, excess dNTPs were removed from the reaction by incubation with 0.3 U shrimp alkaline phosphatase (USB) at 37° C. for 20 minutes followed by a 5 minute incubation at 85° C. to deactivate the enzyme. Single primer extension over the SNP or insertion/deletion were performed at a final concentration of: 600 nM each extension primer, 50 uM d/ddNTP and 0.126 U Thermosequenase (Solis Biodyne) and were incubated at 94° C. for 2 minutes followed by 45 cycles of 94° C. for 5 seconds, 52° C. for 5 seconds, and 72° C. for 5 seconds. The extension primers used were designed by the MALDI-TOF Harvard Core Facility for each p53 mutation studied, using MassArray Assay Design software version 3.1.2.2. The primers used for each mutation were:

```
p53_sw480:    CAGGACAGGCACAAACA;     (SEQ ID NO: 8)
p53_CT7:      AGGACAGGCACAAACAC;     (SEQ ID NO: 9)
p53_DU145:    ACAGCTTTGAGGTGCGT;     (SEQ ID NO: 10)
KRAS_SW480:   TGTGGTAGTTGGACCTG;     (SEQ ID NO: 11)
KRAS_A549:    ACTCTTGCCTACGCCAC.     (SEQ ID NO: 12)
```

The reaction was then desalted by addition of a cation exchange resin followed by mixing and centrifugation to settle the contents of the tube. The extension product was spotted onto a 384 well spectroCHIP before being run on the MALDI-TOF mass spectrometer (Sequenom).

The results are illustrated in Table I. The mutation enrichment factor is listed on the third column of Table I. The enrichment is calculated by comparison to the values obtained when regular PCR MALDI-TOF is applied. Enrichment factors of 10-60 are obtained for the majority of the mutations studied. The enrichment increases as the ratio of mutant-to-wild-type decreases, indicating a non-linear dependence of the enrichment factor on initial concentration of mutations.

TABLE I p53 mutations % mutant or w. type allele for various p53 exon 8 mutations are indicated

| p53 exon 8 mutation = 14484G > A | MALDI-TOF RESULT | | ENRICHMENT-PCR |
|---|---|---|---|
| CELL LINE DILUTIONS SCREENED | % A mutant | % G w. type | ENRICHMENT |
| SW480-w. type ratio 1:5 regular PCR | 15 | 85 | |
| SW480-w. type ratio 1:10 regular PCR | 5 (MassSpec limit) | 95 | |
| SW480-w. type ratio 1:33 regular PCR | 0 | 100 | |
| SW480-w. type ratio 1:10 CO.L.D-PCR | 45 | 55 | ~9 |
| SW480-w. type ratio 1:100 CO.L.D-PCR | 33 | 67 | >10 |
| SW480-w. type ratio 1:300 CO.L.D-PCR | 31 | 69 | >30 |
| WILD TYPE ONLY, CO.L.D-PCR | 0 | 100 | None |

| p53 exon 8 mutation = 14483C > T | MALDI-TOF RESULT | | CO.L.D-PCR |
|---|---|---|---|
| CELL LINE DILUTIONS SCREENED | % T mutant | % C w. type | ENRICHMENT |
| CT7-w. type ratio 1:5 regular PCR | 28 | 72 | N/A |
| CT7-w. type ratio 1:10 regular PCR | 18 | 82 | N/A |
| CT7-w. type ratio 1:33 regular PCR | 5 (MassSpec limit) | 95 | N/A |
| CT7-w. type ratio 1:100 CO.L.D-PCR | 45 | 54 | ~18 |
| CT7-w. type ratio 1:200 CO.L.D-PCR | 28 | 72 | ~40 |
| CT7-w. type ratio 1:300 CO.L.D-PCR | 27 | 73 | ~60 |
| WILD TYPE ONLY, CO.L.D-PCR | 0 | 100 | None |

| p53 exon 8 mutation = 14486G > T | MALDI-TOF RESULT | | CO.L.D-PCR |
|---|---|---|---|
| CELL LINE DILUTIONS SCREENED | % G mutant | % T w. type | ENRICHMENT |
| DU145-w. type ratio 1:5 regular PCR | 28 | 72 | N/A |
| DU145-w. type ratio 1:10 regular PCR | 18 | 82 | N/A |
| DU145-w. type ratio 1:33 regular PCR | 0 | 100 | N/A |
| DU145-w. type ratio 1:33 CO.L.D-PCR | 27 | 73 | ~7 |
| DU145-w. type ratio 1:100 CO.L.D-PCR | 12 | 88 | >10 |
| DU145-w. type ratio 1:300 CO.L.D-PCR | 0 | 100 | undetectable |
| WILD TYPE ONLY, CO.L.D-PCR | 0 | 100 | None |

Kras mutations
% mutant or w. type allele for Kras codon 12 mutations are indicated

| Kras codon 12 mutation = GGT > AGT | MALDI-TOF RESULT | | CO.L.D-PCR |
|---|---|---|---|
| CELL LINE DILUTIONS SCREENED | % A mutant | % G w. type | ENRICHMENT |
| A549-w. type ratio 1:10 regular PCR | 25 | 75 | N/A |
| A549-w. type ratio 1:33 CO.L.D-PCR | 40 | 60 | ~5.5 |
| A549-w. type ratio 1:100 CO.L.D-PCR | 25 | 75 | ~10 |
| A549-w. type ratio 1:200 CO.L.D-PCR | 12 | 88 | ~10 |

| Kras codon 12 mutation = GGT > GTT | | | CO.L.D-PCR |
|---|---|---|---|
| CELL LINE DILUTIONS SCREENED | % A mutant | % G w. type | ENRICHMENT |
| SW480-w. type ratio 1:10 regular PCR | 15 | 85 | N/A |
| SW48-w. type ratio 1:33 CO.L.D-PCR | 15 | 85 | ~3 |
| SW48-w. type ratio 1:100 CO.L.D-PCR | 7 | 93 | ~5 |
| SW48-w. type ratio 1:200 CO.L.D-PCR | 5 | 95 | ~7 |
| WILD TYPE ONLY, CO.L.D-PCR | 0 | 100 | None |

Comparison of ENRICHMENT-PCR-MALDI-TOF with regular-PCR-MALDI-TOF.
The mutation enrichment gained is listed on the last column.

Example 6

Comparison of TAQMAN Based Regular Real-Time PCR and Enrichment Based Real-Time PCR Nucleic acid amplification reactions were performed to compare TAQMAN probe assays in regular real-time and an enrichment based real-time PCR. To compare the two real-time detection methods both genomic DNA and clinical tumor samples having a G>A mutation in p53 exon 8 were assayed at various dilutions in wild-type sequence. Serial dilutions (1:3, 1:10, 1:30, 1:100 and 1:300) of genomic DNA from SW480 into wild-type DNA were made. Specifically, real time PCR reactions were performed directly from 20 ng genomic DNA in the presence of 0.2 µM Taqman probe 5'-6-Fam-TTT GAG GTG CAT GTT TGT GCC-BHQ_1-3' (SEQ ID NO: 13) that fully matches the p53 mutation-containing sequence on DNA from SW480 cells. Final concentrations of other reagents were: 1× GoTaq Flexi buffer (Promega), 1× GoTaq polymerase (Promega) 0.2 mM each dNTP, 0.2 µM forward primer, 5'-TGG TAA TCT ACT GGG ACG-3' (SEQ ID NO: 3), 0.2 µM reverse primer, 5'-CGG AGA TTC TCT TCC TCT-3' (SEQ ID NO: 4), $MgCL_2$ 3 mM, plus DNA. The size of the PCR amplicon was 87 by and Tc=83.5° C. Fast COLD-PCR cycling was: 95° C., 120 sec; (95° C., 15 sec; 58° C. fluorescence reading ON, 60 sec)×25 cycles; (83.5° C. 15 sec; 58° C. fluorescence reading ON, 60 sec)×25 cycles. For Regular PCR cycling, the same program was employed, but the denaturation temperature throughout PCR was 95° C. Experiments were repeated at least 5 times in independent experiments.

Figure 8:
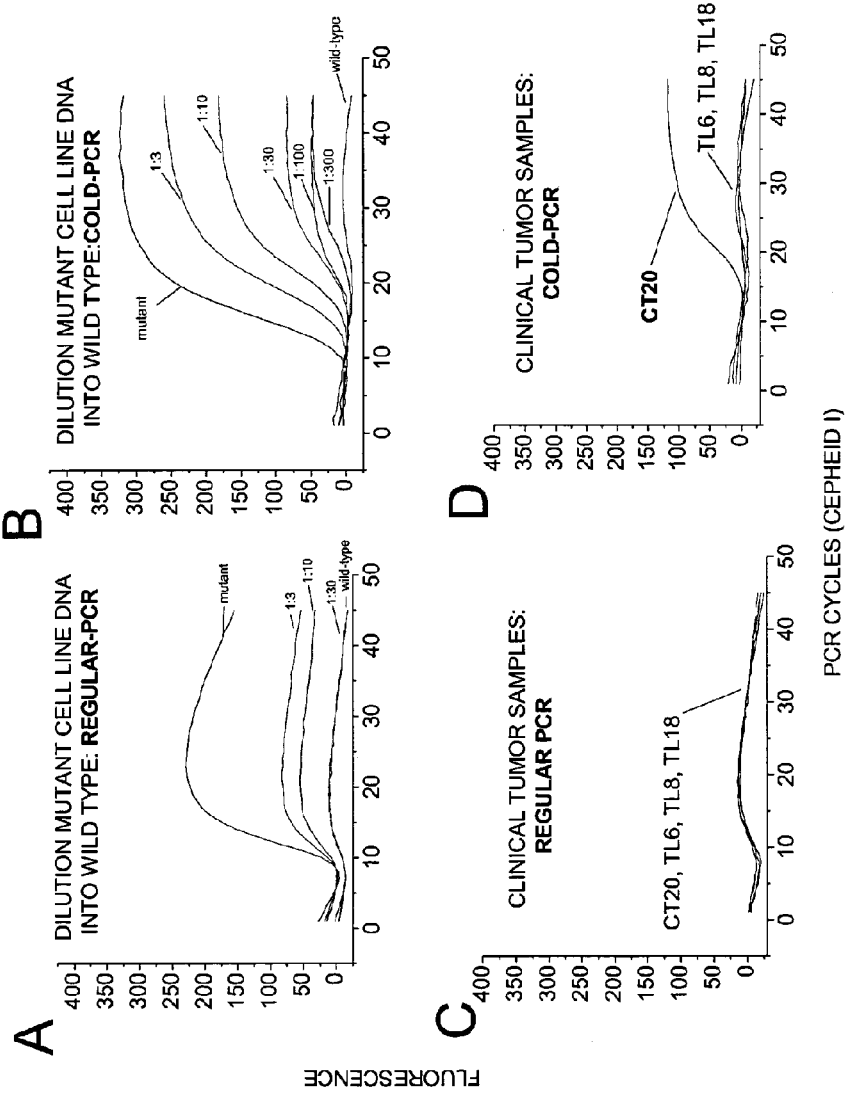
FIG. 8A-8D illustrates amplification plots for wild-type and mutant p53 exon 8 in regular real-time PCR or via an enrichment method of the invention applied in a real-time format. (a) shows amplification plots in regular real-time PCR for serially diluted cell lines containing a mutant in p53 exon 8 mutation. (b) shows amplification plots in an enrichment procedure of the invention as applied in a real-time PCR format for serially diluted cell lines containing a mutant in p53 exon 8 mutation. (c) shows amplification plots in regular real-time PCR of four clinical tumor samples one of which is known to contain a p53 exon 8 mutation (CT20). (d) shows amplification plots for an enrichment procedure of the invention as applied in a real-time PCR format for the four clinical tumor samples.

Amplification plots illustrating the sensitivity of regular and enriched real-time PCR as applied to genomic DNA from the colon cancer cell line SW480 are depicted in FIGS. 8A and 8B. FIG. 8B demonstrates that enriched real-time PCR can detect the presence of the mutation at a 1:300 mutant to wild-type allele ratio. In contrast, regular real-time PCR conducted under identical conditions, with the exception of the Tc step, can only detect the mutant at maximum dilution of 1:10 (FIG. 8A). Therefore, the sensitivity of the assay is 30 fold better using the enrichment procedure.

Amplification plots comparing the sensitivity of regular and enriched real-time PCR in clinical tumor samples having the p53 exon 8 mutation (one of which is know to contain a low level mutation (5% mutant to wild-type) in p53 exon 8, CT20) are illustrated in FIGS. 8C and 8D. Enriched real-time PCR was readily able to detect the mutation (FIG. 8D), while regular PCR did not (FIG. 8C). The remaining sample (TL6, TL8 and TL18), which were known to be wild type samples, did not amplify (FIG. 8C) under the same conditions.

Example 7

Mutation Scanning Via Enrichment Real-Time PCR

Nucleic acid amplification reaction mixtures were created to compare the ability of regular and enriched real-time PCR utilizing DNA detection dyes to detect samples containing mutations anywhere along exon 8 of p53. The method provides for a fast and convenient method to identify unknown mutations or heterozygous SNPs. Thus, the present method can be adapted by one of ordinary skill in the art to scan large numbers of genes for germline or somatic mutations for a variety of different applications (e.g. scanning for BRCA1/2 mutations in populations at high risk for developing breast/ovarian CA, scanning entire genetic pathways for identifying mutations, etc).

Figure 9:
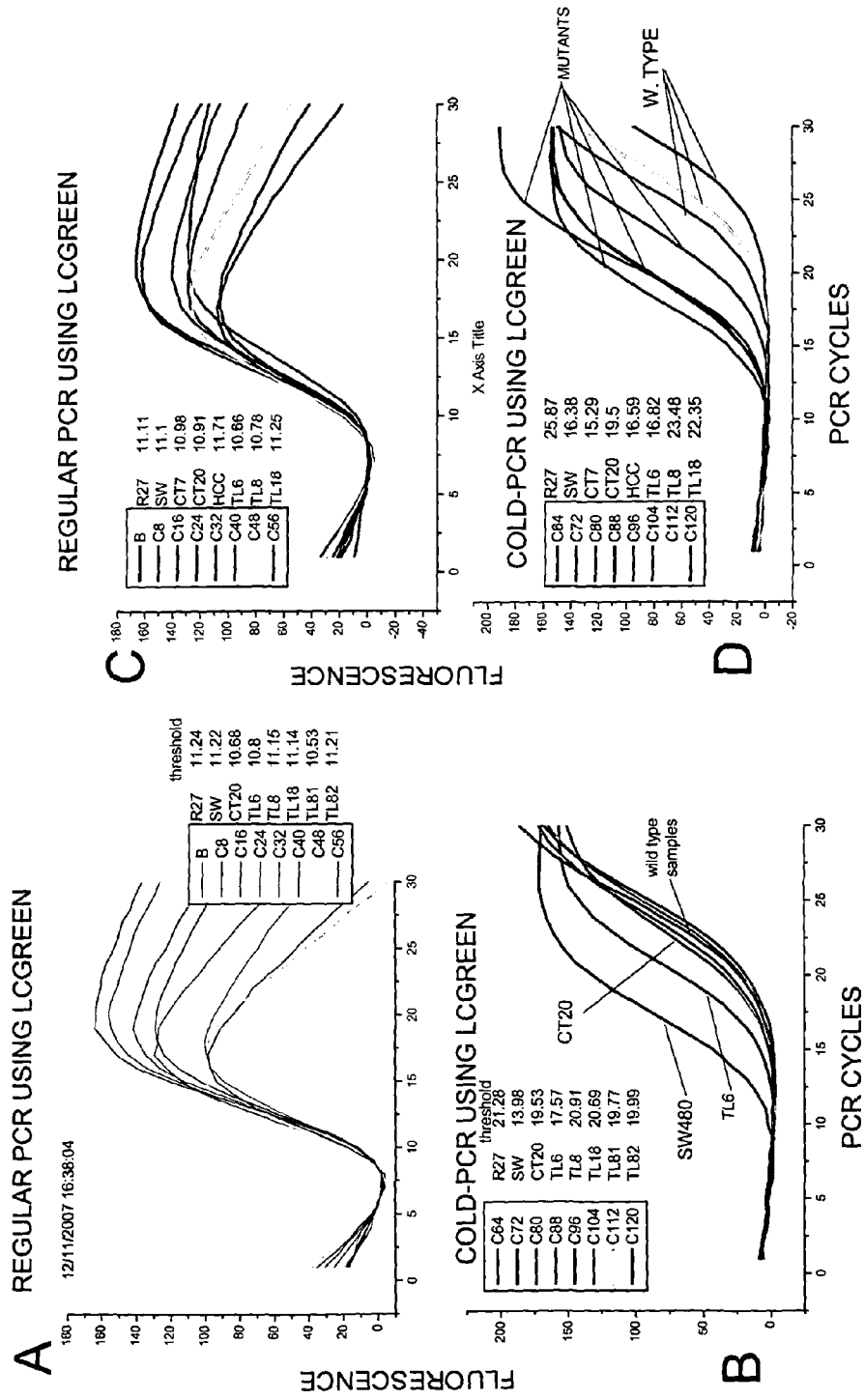
FIG. 9A-D regular and enriched real-time PCR amplification plots for wild-type and mutant p53, exon 8 utilizing a DNA detection dye (LCGreen). (a) shows amplification plots for regular real-time PCR of mutant (SW480, TL6, CT20) and wild-type (R27, TL8, TL18, TL81, TL82) p53, exon 8 containing samples. (b) shows amplification plots from an enrichment procedure of the invention as applied in a real-time format for mutant (SW480, TL6, CT20) and wild-type (R27, TL8, TL18, TL81, TL82) p53, exon 8 containing samples. (c) shows amplification plots for regular real-time PCR for mutant (SW480, CT7, HCC, CT20) and wild-type p53, exon 8 containing samples. (d) shows amplification plots for an enrichment procedure of the invention as applied in a real-time format for mutant (SW480, CT7, HCC, CT20) and wild-type p53, exon 8 containing samples.

FIGS. 9A and 9B illustrate amplification plots comparing both regular and enriched real-time PCR using LC-Green dye in a variety of cell lines and clinical samples that are known to contain mutations in exon 8 of p53. The data shows that real-time regular-PCR (FIG. 9A) is unable to distinguish between the mutant (SW480, TL6 and CT20) and wild-type (R27, TL8, TL18, TL81 and TL82) samples, while enriched real-time PCR does (FIG. 9B). The enrichment method provides earlier threshold detection for the mutation containing samples than for the wild-type samples.

FIGS. 9C and 9D illustrates the results from amplification reactions prepare under reaction conditions identical to those illustrated in FIGS. 9A and 9B but here the samples are all lung tumors. The data shows that real-time regular-PCR (FIG. 9C) can not differentiate between the mutant and wild-type samples, while real-time enriched PCR (FIG. 9D) does. The enrichment method provides earlier threshold detection for the mutation containing samples than for the wild-type samples.

Further, the enriched detection method was able to identify a previously unknown C>T mutation in sample TL6.

Example 8

Organic Solvents Increase Enrichment of Mutations During Regular and Enhanced Real-Time PCR Nucleic acid amplification reaction mixtures were prepared to assess the impact of organic solvents on regular and enriched real-time PCR. Reactions were performed either in the presence or the absence of an organic solvent (3% DMSO). The procedure used was the same as that described in Example 7 and depicted in FIGS. 9C and 9D except for the addition of 3% DMSO.

Figure 10:
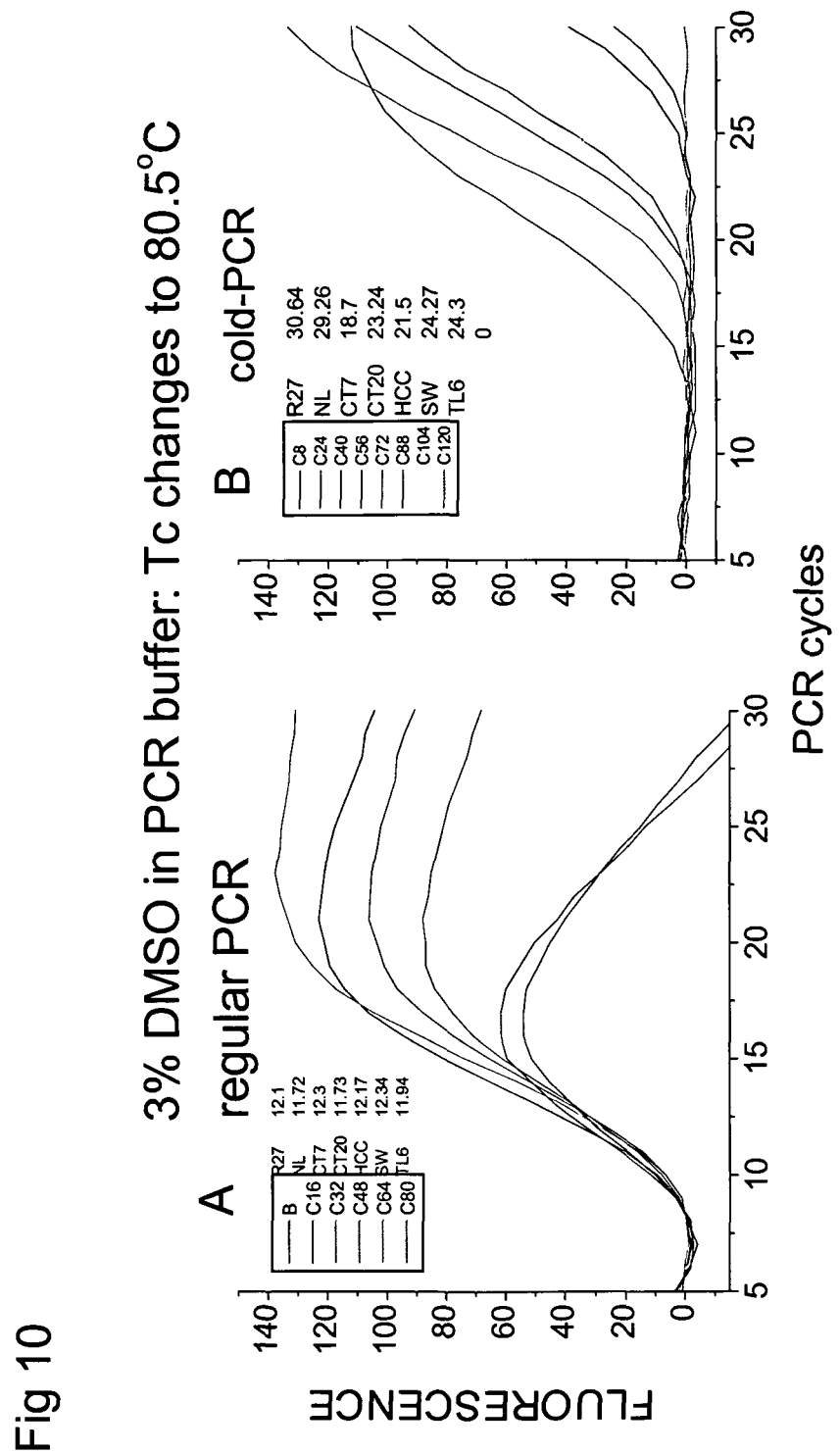
FIG. 10A-B illustrates the impact of organic solvents (e.g., 3% DMSO) on target enrichment. (a) amplification plots in real-time PCR for wild-type and mutant p53 exon 8. (b) amplification plots of an enrichment procedure of the invention as applied in a real-time format for mutant and wild-type p53 exon 8.

The presence of the organic solvent enhanced discrimination between the amplification plots of samples containing the mutated sequences with those containing wild-type sequences (FIG. 10). For example, the threshold difference between wild-type samples and mutant samples increased from ~5-cycles (real-time enrichment without DMSO, see FIG. 9A) to more than 10 cycles (real-time enrichment with DMSO, see FIG. 10A).

Example 9

Detection of Ultra-Low Level Mutations Using RFLP Combined with Enrichment PCR Enrichment PCR combined with RFLP-PCR can be used for improved identification of ultra-low-level mutations, e.g. for identifying random mutations in a cancer genome or resistance mutations in cancer samples at a very early stage, i.e. before treatment.

Figure 11:
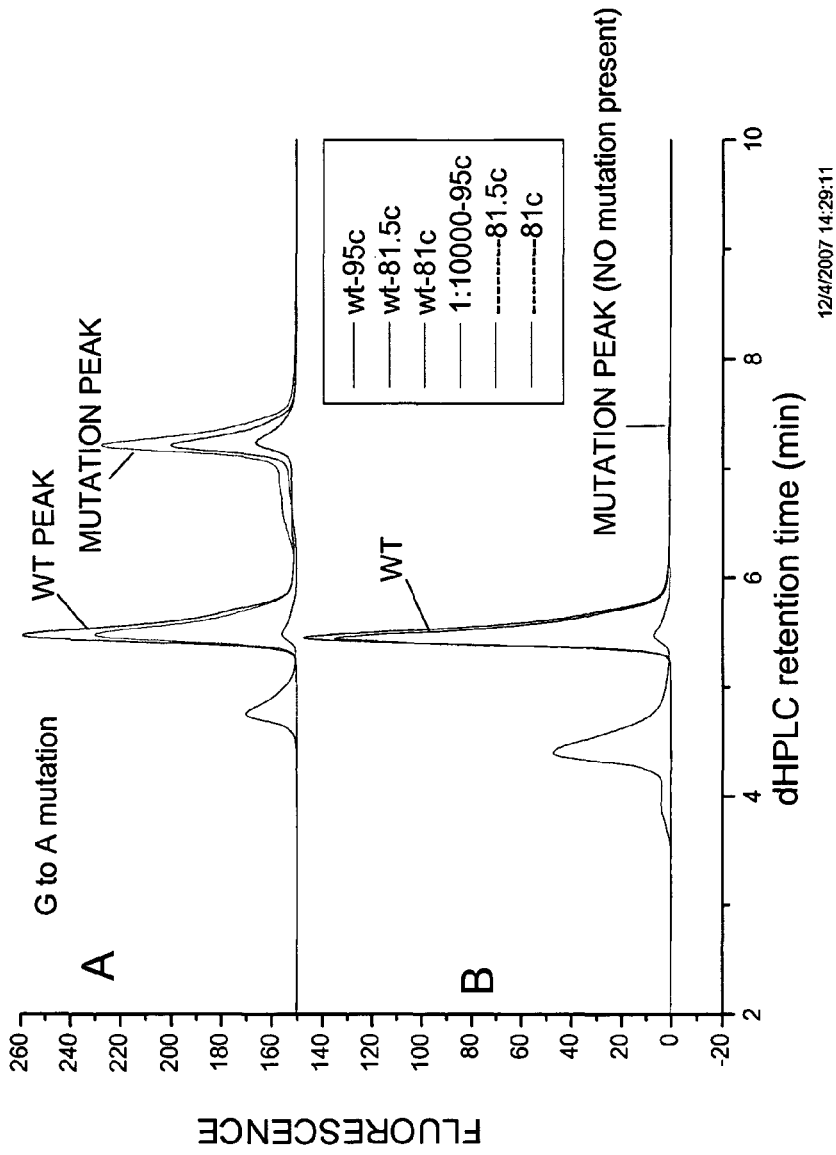
FIG. 11 illustrates improved Restriction Fragment Length Polymorphism (RFLP) detection using an enrichment procedure of the invention following Taq1 digestion of the AA761 EGFR mutation. (a) illustrates the detection of wild-type and mutant (AA761) EGFR when diluted 1:10,000 (mutant:genome) after regular PCR or an enrichment procedure. (b) illustrates the detection of wild-type EGFR as assayed by regular PCR.

For example, samples containing wild-type EGFR exon 19 were selectively digested with TaqI enzyme. Dilutions of up to 1:10,000 mutant-to-genomic DNA were then subjected to PCR either in an enrichment format (Tc=81.5 or 81° C.) or in regular-PCR format (95° C.). The enrichment of the mutation was quantified by TaqI digestion followed by dHPLC (FIG. 11). The amount of mutation present was quantified by the presence of a separate mutation peak at retention time of about 7 min. Following the enrichment procedure the mutation peak is much more evident than following regular-PCR. In conclusion, the enrichment procedure substantially improved the detection of very low level mutations identified via RFLP-PCR.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

I claim:

1. A method for enriching a target nucleic acid sequence in a reaction mixture, said method comprising:
   a. subjecting a reaction mixture suspected of having a target sequence duplex and a reference sequence duplex to a first denaturing temperature that is above the melting temperature ($T_m$) of the target sequence duplex and the reference sequence duplex so as to permit the denaturation of said target sequence duplex and said reference sequence duplex to form target strands and reference strands, wherein said target sequence duplex comprises one or more insertion, deletion or substitution and differs by at least one nucleotide from said reference sequence duplex and is amplifiable by the same primer pair as said reference sequence duplex;
   b. reducing the temperature of the reaction mixture so as to permit formation of target strand/reference strand duplexes;
   c. subjecting said reaction mixture to a critical temperature ($T_c$) that is below the $T_m$ of said reference sequence duplex so as to permit the preferential denaturation of said duplex of step (b) to form denatured target and reference strands;
   d. reducing the temperature of the reaction mixture so as to permit said primer pair to anneal to said target and reference strands; and
   e. extending said primer pair so as to enrich said target sequence relative to said reference sequence.

2. A method of enriching a target sequence as recited in claim 1 further comprising:
   alternatively repeating one or more times the steps b) and c) before executing step d).

3. The method of claim 1 wherein said target and reference sequences are first amplified by subjecting the reaction mixture to PCR and then subjecting at least a portion of the reaction mixture to the enrichment method of claim 1.

4. The method of claim 1 wherein said target sequence is a mutant allele comprising one or more deletions, insertions or alterations.

5. The method of claim 1 wherein said target sequence is differentially methylated from the reference sequence.

6. The method of claim 1 wherein said target and reference sequences comprise at least 25 bases.

7. The method of claim 1 wherein said $T_c$ is 0.3° C.–5° C. below the Tm of said reference sequence duplex.

8. The method of claim 1 wherein the $T_c$ is below the melting temperature of the target sequence duplex.

9. The method of claim 1 wherein said method is repeated for two or more cycles.

10. The method of claim 1 further comprising the step of analyzing said reaction mixture with enriched target sequence using one or more of the methods selected from the group consisting of: MALDI-TOF, HR-Melting, Di-deoxy-sequencing, Single-molecule sequencing, pyrosequencing, SSCP, RFLP, dHPLC, CCM, digital PCR and quantitative-PCR.

11. The method of claim 1 wherein said $T_c$ is applied for 1 second-5 minutes.

12. The method of claim 1 wherein said reaction mixture contains a nucleic acid detection dye.

13. The method of claim 12 wherein said method is performed in a real-time PCR device.

14. The method of claim 1 performed under real-time reaction conditions utilizing a labeled probe.

15. A computer readable medium comprising program instructions for performing the method of claim 1.

16. The method of claim 1 wherein said method is used to enrich two or more different target sequences and said method further comprises one or more additional pairs of primers specific to said different target sequences.

17. The method of claim 1 wherein said primer pair has a melting temperature that is below the temperature applied in step (b).

18. The method of claim 16 wherein the melting temperature of said primer pairs are at least 5° C. below the temperature in step (b).

19. The method of claim 1 wherein the reaction mixture includes a modified nucleic acid.

20. The method of claim 1, wherein said method is repeated for two or more cycles.

21. The method of claim 1, wherein said method is repeated for between 5 and 40 cycles.

22. The method of claim 1, wherein said method is repeated for between 10 and 30 cycles.

23. The method of claim 5, wherein prior to implementing the method of claim 1 on the reaction mixture, the reaction mixture is treated with sodium bisulfite.

24. The method of claim 1, wherein the target sequence is at least 70% homologous to the reference sequence.

25. The method of claim 1, wherein the target sequence is at least 80% homologous to the reference sequence.

26. The method of claim 1, wherein the target sequence and the reference sequence differ by between 1 and 10 nucleotides.

* * * * *

(12) EX PARTE REEXAMINATION CERTIFICATE (10722nd)

United States Patent
Makrigiorgos

(10) Number: US 8,455,190 C1
(45) Certificate Issued: Sep. 29, 2015

(54) ENRICHMENT OF A TARGET SEQUENCE

(75) Inventor: Gerassimos Makrigiorgos, Chestnut Hill, MA (US)

(73) Assignee: DANA-FARBER CANCER INSTITUTE, INC., Boston, MA (US)

Reexamination Request:
No. 90/013,355, Sep. 28, 2014

Reexamination Certificate for:
Patent No.: 8,455,190
Issued: Jun. 4, 2013
Appl. No.: 12/671,295
PCT Filed: Jul. 31, 2008
PCT No.: PCT/US2008/009248
§ 371 (c)(1),
(2), (4) Date: Mar. 18, 2010
PCT Pub. No.: WO2009/017784
PCT Pub. Date: Feb. 5, 2009

Related U.S. Application Data

(60) Provisional application No. 60/962,838, filed on Aug. 1, 2007.

(51) Int. Cl.
*C12Q 1/68* (2006.01)
*C07H 21/02* (2006.01)
*C07H 21/04* (2006.01)
*C07H 21/00* (2006.01)

(52) U.S. Cl.
CPC ............ *C12Q 1/6848* (2013.01); *C12Q 1/6858* (2013.01); *C12Q 2527/107* (2013.01); *C12Q 2545/107* (2013.01)

(58) Field of Classification Search
None
See application file for complete search history.

(56) References Cited

To view the complete listing of prior art documents cited during the proceeding for Reexamination Control Number 90/013,355, please refer to the USPTO's public Patent Application Information Retrieval (PAIR) system under the Display References tab.

*Primary Examiner* — Bruce Campell

(57) ABSTRACT

The present invention is directed to methods, compositions, software and devices for enriching low abundance alleles from a sample. The method is based in part on a modified nucleic acid amplification protocol that includes incubating the reaction mixture at a critical denaturing temperature or "Tc". By employing the present invention the current detection limits of all PCR-based technologies are greatly improved.

**EX PARTE
REEXAMINATION CERTIFICATE**

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-26 is confirmed.

New claims 27-32 are added and determined to be patentable.

27. *A method for enriching a target nucleic acid sequence in a reaction mixture, said method comprising:*
   a. *subjecting a reaction mixture suspected of having a target sequence duplex and a reference sequence duplex to a first denaturing temperature that is above the melting temperature ($T_m$) of the target sequence duplex and the reference sequence duplex so as to permit the denaturation of said target sequence duplex and said reference sequence duplex to form target strands and reference strands, wherein said target sequence duplex comprises one or more insertion, deletion or substitution and differs by at least one nucleotide from said reference sequence duplex and is amplifiable by the same primer pair as said reference sequence duplex;*
   b. *reducing the temperature of the reaction mixture to a temperature above the $T_m$ of said primer pair so as to permit formation of target strand/reference strand duplexes while preventing binding of said primer pair to the target and reference sequences;*
   c. *subjecting said reaction mixture to a critical temperature ($T_c$) that is below the $T_m$ of said reference sequence duplex so as to permit the preferential denaturation of said duplex of step (b) to form denatured target and reference strands;*
   d. *reducing the temperature of the reaction mixture so as to permit said primer pair to anneal to said target and reference strands; and*
   e. *extending said primer pair so as to enrich said target sequence relative to said reference sequence.*

28. *The method of claim 27, further comprising: alternatively repeating one or more times the steps b) and c) before executing step d).*

29. *The method of claim 27, wherein said target and reference sequences are first amplified by subjecting the reaction mixture to PCR and then subjecting at least a portion of the reaction mixture to the enrichment method of claim 27.*

30. *The method of claim 27, wherein said method is repeated for two or more cycles.*

31. *The method of claim 30, wherein said method is repeated for between 5 and 40 cycles.*

32. *The method of claim 30, wherein said method is repeated for between 10 and 30 cycles.*

\* \* \* \* \*